(12) United States Patent
Childre et al.

(10) Patent No.: US 7,163,512 B1
(45) Date of Patent: Jan. 16, 2007

(54) METHOD AND APPARATUS FOR FACILITATING PHYSIOLOGICAL COHERENCE AND AUTONOMIC BALANCE

(75) Inventors: Doc L. Childre, Boulder Creek, CA (US); Rollin McCraty, Boulder Creek, CA (US); Michael A. Atkinson, Boulder Creek, CA (US)

(73) Assignee: Quantum Intech, Inc., Boulder Creek, CA (US)

( * ) Notice: Subject to any disclaimer, the term of this patent is extended or adjusted under 35 U.S.C. 154(b) by 0 days.

(21) Appl. No.: 10/486,775

(22) PCT Filed: Mar. 1, 2000

(86) PCT No.: PCT/US00/05224

§ 371 (c)(1),
(2), (4) Date: Feb. 13, 2004

(87) PCT Pub. No.: WO00/51677

PCT Pub. Date: Sep. 6, 2000

(51) Int. Cl.
*A61B 5/0482* (2006.01)
*A61B 5/02* (2006.01)
*A61M 21/00* (2006.01)

(52) U.S. Cl. .................... 600/500; 600/545; 600/26
(58) Field of Classification Search ........ 600/485–505, 600/529–538, 544–547
See application file for complete search history.

(56) References Cited

U.S. PATENT DOCUMENTS 5,356,368 A * 10/1994 Monroe ................... 600/28
5,694,939 A * 12/1997 Cowings ................. 600/484
5,800,337 A * 9/1998 Gavish .................... 600/27
6,067,468 A * 5/2000 Korenman et al. ........ 600/547
6,358,201 B1 * 3/2002 Childre et al. ............ 600/300
6,390,986 B1 * 5/2002 Curcie et al. ............. 600/485

OTHER PUBLICATIONS

William Tiller et al, "Cardiac Coherence: A New Noninvasive Measure of Autonomic Nervous System Order," Alternative Therapies, Jan. 1996, vol. 2, No. 1, p. 52-63.*

* cited by examiner

*Primary Examiner*—Robert L Nasser
(74) *Attorney, Agent, or Firm*—Crowell & Moring

(57) ABSTRACT

Method and apparatus for determining the state of entrainment between biological systems which exhibit oscillatory behavior such as heart rhythms, respiration, blood pressure waves and low frequency brain waves based on a determination of heart rate variability (HRV) and an evaluation of the power spectrum thereof. Entrainment reflects a harmonious balance between the two branches of the autonomic nervous system within the body. This internal state of heightened physiological efficiency enhances health and promotes optimal performance. According to one embodiment a method is used to determine the entrainment level based on an entrainment parameter related to HRV. The method first determines the power distribution spectrum (PSD) and then calculates an entrainment parameter (EP), which is a measure of the power distribution in the HRV spectrum. High EP values occur when this power is concentrated within a relatively narrow range of frequencies, and lower values when the power is distributed over a broader range of frequencies. In one embodiment, an apparatus is provided for monitoring the heart beat and presenting this information via a personal computer, handheld device, or other processing means.

37 Claims, 19 Drawing Sheets

BASELINE

DISORDERED

ENTRAINMENT

FIG. 8A
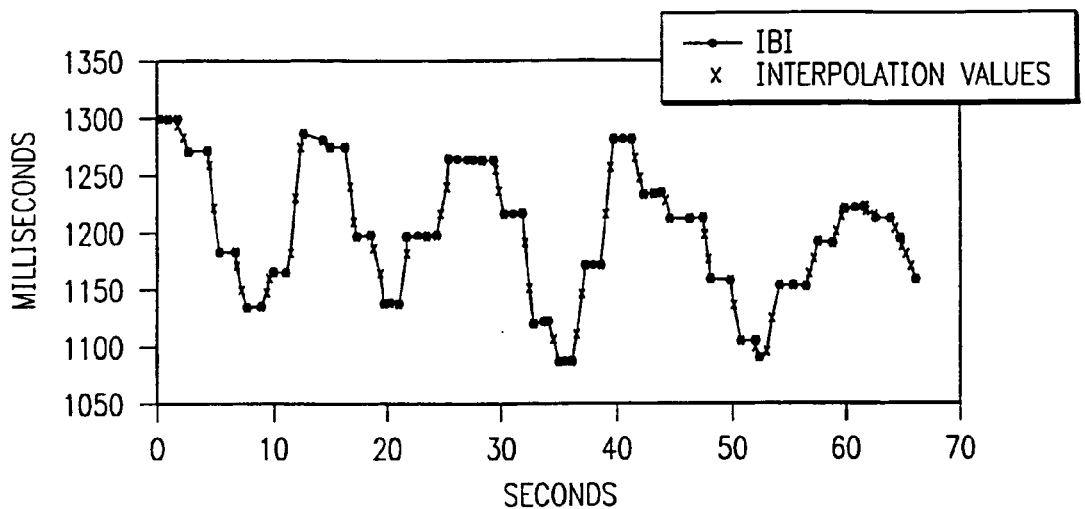
FIG. 8B
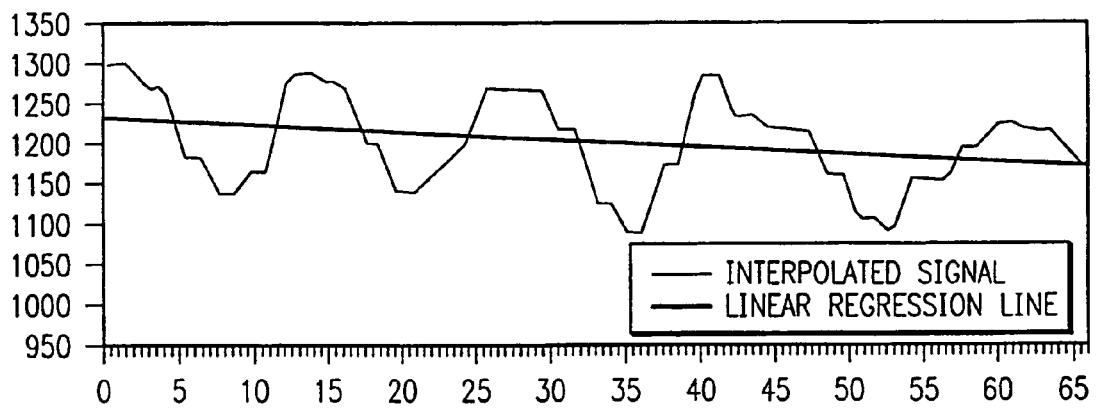
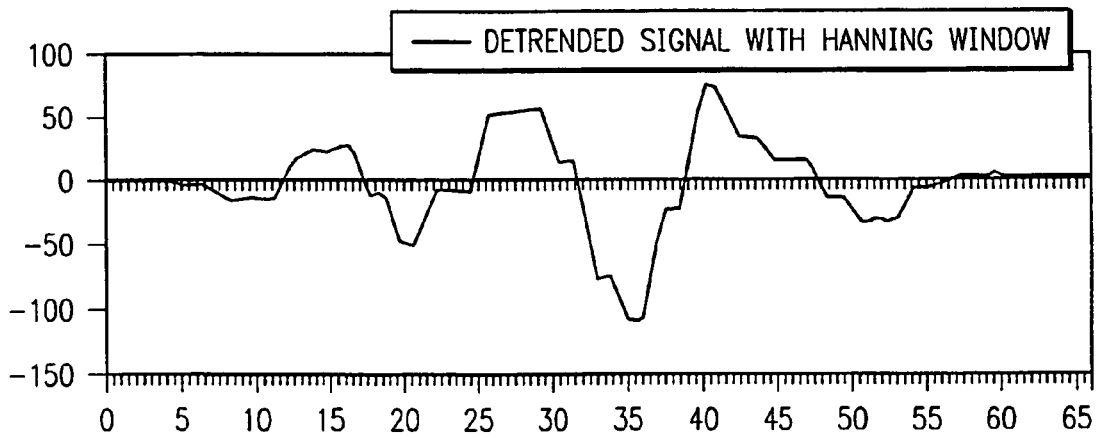
FIG. 8C

METHOD AND APPARATUS FOR FACILITATING PHYSIOLOGICAL COHERENCE AND AUTONOMIC BALANCE

CROSS REFERENCE TO RELATED APPLICATIONS

This application is a 371 of PCT International Application No. PCT/US00/05224, filed on Mar. 1, 2000, which claims the benefit of U.S. patent application Ser. No. 09/260,643, filed on Mar. 2, 1999, now U.S. Pat. No. 6,358,201.

TECHNICAL FIELD

The present invention relates generally to the evaluation of heart rate variability, and specifically to the analysis of the power spectrum distribution thereof.

BACKGROUND ART

With the growing complexity of life, the relation between physiological conditions and emotional health becomes of increasing interest. Many studies have shown that stress and other emotional factors increase the risk of disease, reduce performance and productivity and severely restrict the quality of life. To this end, the medical communities around the world continually seek remedies and preventive plans. Recently a focus on the self-regulation of systems within the body has led to research in the areas of biofeedback, etc.

In the last 25 years, a variety of new techniques have been introduced as alternatives to more traditional psychotherapies or pharmaceutical interventions for improving mental and/or emotional imbalances. In addition to the more psychological approaches like cognitive re-structuring and neurolinguistic programming, psychologists have employed several techniques from Eastern cultures to "still the mind" during focused meditation. In yoga, for example, one generally focuses on the breath or parts of the brain, whereas in qigong one focuses on the "dan tien" point (below the navel). In a Freeze Frame® (FF) technique, developed by the Institute of Heart Math in Boulder Creek, Calif., one focuses attention on the area around the heart. All these techniques focus attention upon areas of the body which are known to contain separate but interacting groups of neuronal processing centers, and biological oscillators with which they interact. The heart, brain, and the intestines contain biological oscillators known as pacemaker cells. By intentionally focusing attention on any one of these oscillator systems, one can alter its rhythms. This is at least true for the brain (meditation), yogic breathing (respiration), the heart (FF), and most likely the gut (qigong), since it is also regulated by the autonomic nervous system (ANS). The body also contains other oscillating systems such as the smooth muscles of the vascular system. We have previously shown that this system, measured by recording pulse transit time (PTT), as well as the brain, measured by an electroencephalograph (EEG), the heart, measured by a heart rate variability (HRV), and the respiration system, measured by the respiration rate, can all entrain. Furthermore, they all synchronize to a frequency varying around 0.1 Hertz (Hz). Thus, one can intentionally bring these systems, acting as coupled biological oscillators, into synchrony with each other.

The FF technique is a self-management technique by which one focuses on the heart to disengage from moment-to-moment mental and emotional reactions. A study utilizing the FF technique in a psychological intervention program with HIV-positive subjects resulted in significant reductions in life-stress, state and trait anxiety levels, and self-assessed physical symptoms. Two other studies with healthy individuals using the FF technique to enhance positive emotional states showed increased salivary IgA and increased sympathovagal balance. Increased sympathovagal balance is known to protect against detrimental physiological effects associated with overactive sympathetic outflow from the brain. Other studies have shown the techniques to be effective in improving autonomic balance and decreasing the stress hormone cortisol and increasing DHEA, improving glycemic regulation in diabetics, reducing blood pressure in hypertensive individuals and significantly reducing psychological stressors such as anxiety, depression, fatigue and overwhelm in many diverse populations.

Sympathovagal balance has been measured using various techniques. For example, individuals can be trained to consciously control their heart rate using biofeedback techniques. However, the enhanced parasympathetic activity is probably mediated through control of respiration. Neutral hypnosis and operant conditioning of heart rate have been demonstrated to decrease in the sympathetic/parasympathetic ratio by increasing parasympathetic activity independent of controlled breathing techniques. The FF technique does not require biofeedback equipment nor does it require conscious control of respiration although a short breathing protocol is used this technique. Our results suggest that emotional experiences play a role in determining sympathovagal balance independent of heart rate and respiration. The shifts in sympathovagal balance toward increased low-frequency (LF) and high frequency (HF) power (measures of heart rate variability) were physiological manifestations of experiencing the emotional state of appreciation. The FF technique focuses on genuinely experiencing the feelings of sincere appreciation or love, in contrast to visualizing or recalling a previous positive emotional experience.

The results of our studies indicate that relatively short periods of practice of the FF technique and other tools developed by the Institute of HeartMath leads to either an "entrainment" or "internal coherence" mode of heart function (described in greater detail below). Most subjects who are able to maintain these states report that the intrusion of random thoughts is greatly reduced and that it is accompanied by feelings of deep inner peace and heightened intuitive awareness.

We also observed that positive emotional states, which lead to the entrainment mode, generated marked changes in the dynamic beating patterns of the heart. A method for quantifying and analyzing and quantifying these heart rhythms is called analysis of heart rate variability (HRV). The normal resting heart rate in healthy individuals varies dynamically from moment to moment. Heart rate variability, which is derived from the electrocardiogram (ECG) or pulse, is a measure of these naturally occurring beat-to-beat changes in heart rate and is an important indicator of health and fitness. HRV is influenced by a variety of factors, including physical movement, sleep and mental and activity, and is particularly responsive to stress and changes in emotional state. The analysis of HRV can provide important information relative to the function and balance of the autonomic nervous system, as it can distinguish sympathetic from parasympathetic regulation of heart rate. Decreased HRV is also a powerful predictor of future heart disease, increased risk of sudden death, as well as all-cause mortality.

Frequency domain analysis decomposes the heart rate tachogram or waveform into its individual frequency components and quantifies them in terms of their relative intensity, in terms of power spectral density (PSD). By applying spectral analysis techniques to the HRV waveform, its different frequency components, which represent the activity of the sympathetic or parasympathetic branches of the autonomic nervous system, can be discerned. The HRV power spectrum is divided into three frequency ranges or bands: very low frequency (VLF), 0.033 to 0.04 Hz; low frequency (LF), 0.04 to 0.15 Hz; and high frequency (HF), 0.15 to 0.4 Hz.

The high frequency (HF) band is widely accepted as a measure of parasympathetic or vagal activity. The peak in this band corresponds to the heart rate variations related to the respiratory cycle, commonly referred to as respiratory sinus arrhythmia. Reduced parasympathetic activity has been found in individuals under mental or emotional stress, suffering from panic, anxiety or worry and depression.

The low frequency (LF) region can reflect both sympathetic and parasympathetic activity, especially in short-term recordings. Parasympathetic influences are particularly present when respiration rates are below 7 breaths per minute or when an individual takes a deep breath. This region is also called the "baroreceptor range" as it also reflects baroreceptor activity and at times blood pressure wave activity and resonance.

When an individual's HRV pattern and respiration are synchronized or entrained, as can happen spontaneously in states of deep relaxation, sleep or when using techniques to facilitate autonomic balance such as Freeze-Frame and the Heart Lock-In, the frequency at which the entrainment occurs is often near 0.1 Hertz. This falls in the center of the LF band and could be misinterpreted as a large increase in sympathetic activity, when in reality it is primarily due to an increase in parasympathetic activity and vascular resonance. Sophisticated modeling techniques have shown that in normal states, about 50% of the total power in the LF band is explained by neural signals impinging on the sinus node which are generated at a central level, and the majority of the remaining power is due to resonance in the arterial pressure regulation feedback loop. The sympathetic system does not appear to produce rhythms that appear much above frequencies of 0.1 Hz, while the parasympathetic can be observed to operate down to frequencies of 0.05 Hz. Thus, in individuals who have periods of slow respiration rate, parasympathetic activity is modulating the heart rhythms at a frequency that is in the LF band. Therefore, in order to discriminate which of the ANS branches is pumping power into the LF region, both respiration and PTT should be simultaneously recorded and considered.

The increase in LF power while in the entrainment mode may represent increased baroreceptor afferent activity. It has been shown that the LF band reflects increased afferent activity of baroreceptors. The LF band has indeed been shown to reflect baroreceptor reflex sensitivity and is affected by physiological states. Increased baroreceptor activity is known to inhibit sympathetic outflow from the brain to peripheral vascular beds, whereas stress increases sympathetic outflow and inhibits baroreflex activity. The increase in LF power seen during the state of deep sustained appreciation may have important implications for the control of hypertension, since baroreflex sensitivity is reduced in these individuals.

There is a noticeable and obvious transition after the FF intervention to the entrainment mode which can be seen in the HRV waveforms and PSD data. In addition, many subjects report that they are able to use the FF technique while they were in a "tense" conversation with someone and starting to react. Even in these conditions, the HRV waveforms indicate that they were able to shift to and maintain the entrainment state.

From tachogram data, it can be seen that, as one moves from a state of frustration to one of sincere appreciation a transition occurs in the waveforms from a noisy wave of large amplitude to a non-harmonic wave form of similar amplitude (entrainment). We have also identified an additional state we call "amplified peace" to indicate this special emotional state of very deep peace and inner harmony. In this state, the HRV waveform becomes a smaller amplitude wave (internal coherence). In general, the transition in the frequency domain (PSD) is from a wide-band spectrum of moderate amplitude to a narrow-band spectrum around 0.1 Hz of very large amplitude (entrainment) and then to a wide-band spectrum of very small amplitude (internal coherence).

In most individuals, small to near-zero HRV, as just described, is an indicator of a potentially pathological condition or aging because it connotes loss of flexibility of the heart to change in rate or a decreased flow of information in the ANS. However, in trained subjects, it is an indication of exceptional self-management of their emotions and autonomic nervous system because their HRV is normally large and the shift into the internal coherence mode is a result of intentionally entering the amplified peace state. This is very different from a pathological condition underlying lowered HRV (in such cases the HRV is always low). The connection between emotional states and HRV could possibly account for the occasional observation of low HRV in otherwise healthy individuals which has detracted from the clinical utility of HRV analysis for unequivocally predicting disease.

During the condition of internal coherence, the electromagnetic energy field produced by the heart, as seen in a fast Fourier transform (FFT) analysis of an electrocardiogram (ECG) signal, is a clear example of a coherent electromagnetic field. Recent advances in the understanding of the interaction between coherent signals and noise in nonlinear systems has resulted in the prediction that these nonthermal, coherent electromagnetic signals may be detected by cells. Further evidence suggests that coherent electromagnetic fields may have important implications for cellular function. For example, it has been recently demonstrated that nonthermal, extremely low frequency electromagnetic signals may affect intracellular calcium signaling. In addition, coherent electromagnetic fields have been shown to produce substantially greater cellular effects on enzymatic pathways, such as ornithine decarboxylase activity, than incoherent signals. This fact suggests that the state of internal coherence may also affect cellular function and provides a potential link between emotional states, autonomic function, HRV and cellular processes.

Conscious focus of attention and/or positive emotions has been shown to significantly influence HRV and PSD. The results of our research support previous work and suggest that psychological interventions which minimize negative and enhance positive emotional states may significantly impact cardiovascular function.

The results of work in this area demonstrate that sincere feelings of appreciation produce a power spectral shift toward LF and HF activity and imply that 1) the major centers of the body containing biological oscillators can act as coupled electrical oscillators, 2) these oscillators can be brought into synchronized modes of operation via mental and emotional self-control, and 3) the effects on the body of such synchronization are correlated with significant shifts in perception and cardiovascular function. It is suggested that positive emotions lead to alterations in sympathovagal balance which may be beneficial in the treatment of hypertension and reduce the likelihood of sudden death in patients with congestive heart failure and coronary artery disease.

There is a need to provide quantified information regarding the balance of the ANS which is easily used and does not require extensive biofeedback equipment. There is further a need for a mobile method of monitoring this balance for use in everyday life.

DISCLOSURE OF INVENTION

The present invention provides a method of measuring certain body rhythms, and then analyzing this information to indirectly determine the entrainment state which is also reflective of balance between the sympathetic and parasympathetic portions of the autonomic nervous system.

According to one embodiment of the present invention, a method includes the steps of sampling a heart beat of a subject, determining a heart rate variability (HRV) of the heart beat as a function of time (HRV(t)), expressing HRV(t) as a function of frequency (HRV(f)), determining a distribution of frequencies in HRV(f), selecting a peak frequency of HRV(f), determining the energy in said peak frequency ($E_{peak}$), determining the energy in frequencies below said peak frequency ($E_{below}$) and above said peak frequency ($E_{above}$), determining a ratio of $E_{peak}$ to $E_{below}$ and $E_{above}$, and providing to the subject, in a first presentation format, a representation of a first parameter related to said ratio.

According to one aspect of the present invention, an apparatus includes sampling means adapted to sample a heart beat of a subject for a first predetermined time period, a display unit, a processing unit coupled to the sampling means and the display unit, wherein the processing unit is adapted to determine a heart rate variability (HRV) of the heart rate by measuring the interval between each beat during the first predetermined time period, wherein the HRV is a function of time, determine a frequency distribution of the HRV, the frequency distribution having at least one peak, the at least one peak including a first number of frequencies, calculate a first parameter of the frequency distribution of the HRV, wherein the first parameter is a ratio of the area under the at least one peak to the area under the rest of the frequency distribution, and outputting the first parameter to the display unit for presentation to the subject.

According to one aspect of the present invention, a method includes the steps of receiving heart rate variability (HRV) information, the HRV information comprising the time intervals between each heart beat of a subject during a first predetermined time period, expressing the HRV as a function of frequency, determining the power in said HRV over a first range of frequencies, selecting a power peak in said first range of frequencies, calculating a first parameter relating the power in said selected power peak to the power in said HRV over a second range of frequencies, presenting the first parameter to the subject.

BRIEF DESCRIPTION OF DRAWINGS

The present invention may be more fully understood by a description of certain preferred embodiments in conjunction with the attached drawings in which:

FIGS. 8A–8F illustrate the steps of the process of FIGS. 7A–7E;

BEST MODE FOR CARRYING OUT THE INVENTION

Figure 1:
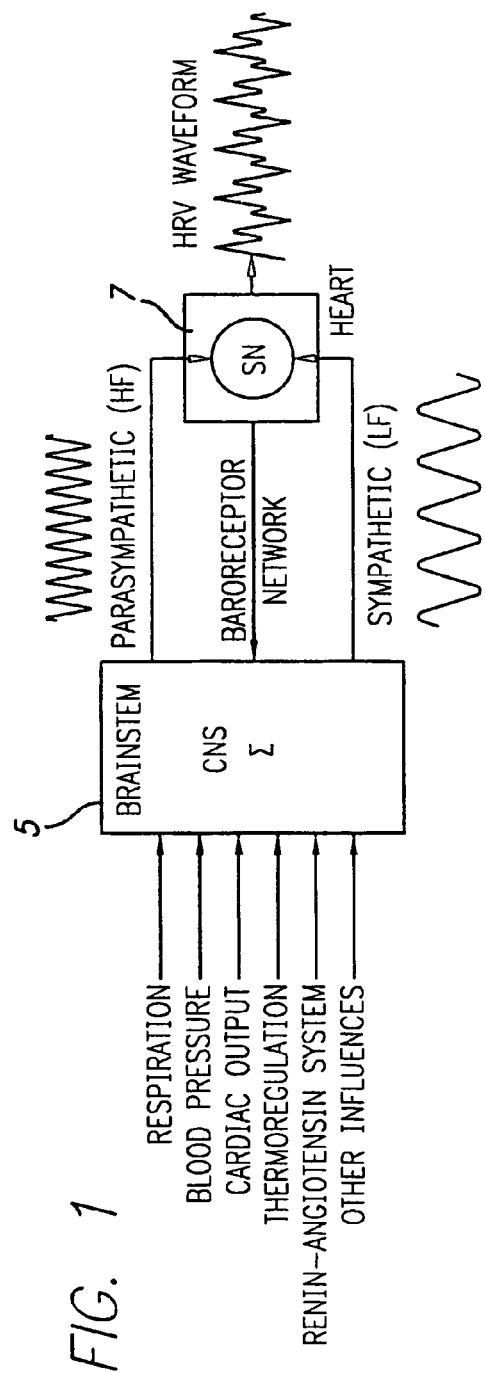
FIG. 1 illustrates in highly diagrammatic form the way in which the sympathetic and parasympathetic subsystems of the autonomic nervous system (ANS) of a higher organism are believed to mutually affect heart rate variability (HRV)

In the following description of the invention and its various aspects and embodiments, we will be using certain terms. For convenience of reference, our preferred definitions thereof are as follows:

As noted above, Freeze-Frame® is one of the tools used in the HeartMath system of self-management. It consists of consciously disengaging the mental and emotional reactions to either external or internal events and then shifting the center of attention from the mind and emotions to the physical area around the heart while focusing on a positive emotion such as love or appreciation. This tool thus allows the individual to shift focus of attention from the mind to the heart. Such a shift results in a wider and more objective perception in the moment.

As used hereafter, the term "appreciation" shall mean the state in which the subject has clear perception or recognition of the feelings of sincere or active appreciation for someone or something. It is the heart-felt feeling of appreciation that is associated with the HRV changes, as contrasted with the mental concept of appreciation which does not appear to produce such HRV changes. The term "amplified peace" shall mean an inner state in which a much deeper state of peace and centeredness is felt than is normally experienced. One also has a sense of standing on the threshold of a new dimension of awareness in this state. There is a sense of inner equilibrium and an awareness that one has accessed a new domain of intuition. As with any experiential state, it is difficult to find words that adequately describe it. This is not a state that one normally walks around in but rather enters for relativity short time periods. However, with practice at staying focused in the heart, the ratios of time in this state can be increased. It can also be described as similar to those moments that one sometimes has when at the beach or in the forest when one feels an especially deep contact with nature or with oneself that is beyond one's normal experience. It is often in these moments that we find the answers to the deeper issues or problems that we experience.

By the term "biological oscillators" we mean cells or groups of cells that produce rhythmic oscillation. When the instantaneous systemic arterial pressure is continuously recorded, fluctuations with each heart beat and with each breath are seen. This rhythmic activity in the autonomic nervous system appears to be supported by at least three biological oscillator systems: 1) centrogenic rhythms in brainstem networks with facultative coupling (entrainment) with the respiratory oscillator, 2) the baroreceptor feedback network, and 3) the autorhythmicity of the vascular smooth muscle. The fact that each of the oscillators can develop different frequencies and that the phase-lags between the oscillations may vary easily explains the general experience that blood pressure waves are quite variable and unpredictable. The existence of several oscillators with similar basic frequencies enables synchronization and entrainment between oscillators. Thus, we can assume that states of regular and steady blood pressure waves are the expression of the entrained action of the complex multi-oscillatory system.

Arterial pulse transit time (PTT) is a measure of the speed of travel of the arterial pulse wave from the heart to some peripheral recording site. It is used as a non-invasive method to monitor the elasticity of the artery walls and to indicate changes in blood pressure on a beat-to-beat basis. The arterial pressure pulse is a wave of pressure which passes rapidly along the arterial system. The pulse wave velocity (4 to 5 m/sec) is much faster than the velocity of blood flow (<0.5 m/sec). The pulse wave velocity varies directly with pressure-related changes in the elasticity of the arterial wall. The more rigid or contracted the arterial wall, the faster the wave velocity. From this, it follows that PTT should vary inversely with blood pressure. Common estimates of the magnitude of this effect indicate that PTT varies by about 1 ms per mm Hg change in pressure.

We will also be describing the results of certain studies conducted in our laboratories. In order to more fully appreciate the nature and conditions of such studies, we wish to describe our key procedures:

For in-the-lab studies, preselected individuals trained in the FF technique are seated in straight, high backed chairs to minimize postural changes, fitted with ECG electrodes, and then given a 10-minute rest period. ECG measurements are recorded during the rest period and the last 5 minutes are used as a baseline period. Recordings are continued while the subjects are asked to utilize the FF technique and consciously focus on a loving state for the next 5 minutes. A selected number of subjects are assessed at each session. After informed consent is obtained, and prior to each session, subjects are asked to refrain from talking, falling asleep, exaggerated body movements or intentionally altering their respiration. Subjects are carefully monitored to ensure there are no exaggerated respiratory or postural changes during the session.

The same subjects are asked to wear ambulatory ECG recorders for a 24-hour period which includes a normal business day in their work place. They are asked to use the FF technique on at least three separate occasions, when they are feeling stress or out of balance. They are instructed to press the recorder's marker button each time they use the FF technique. This portion of a study is designed to assess ANS balance in a real-life stressful environment and to determine the efficacy of the FF technique to consciously improve sympathovagal balance. In general, Ag/AgCl disposable electrodes are used for all bipolar ECG measurements. The positive electrode is located on the left side at the 6th rib, and the reference are placed in the right supraclavicular fossa. Grass model 7P4 amplifiers are used for ECG amplification. Respiration is monitored with a Resp-EZ piezoelectric belt around the chest. A Grass model 80 cardiac microphone is used when the blood pressure wave is recorded for calculation of pulse transit time (PTT). The PTT interval is the time between the peak of the R-wave of the ECG and the appearance of the pulse wave associated with that same cardiac contraction at the index finger on the left hand. In the out-of-lab studies, ambulatory ECG recording is accomplished with a Del Mar Holter recording system model 363.

During the data analysis phase, the HRV waveform is in the form of an R—R interval tachogram. The spectral analysis of this signal is obtained from the successive discrete series of R—R duration values taken from the ECG signal sampled at 256 Hz and FFTed. All data from an in-the-lab study is digitized by a Bio Pac 16 bit digitizer and software system. All post analysis, including FFTs, PSD and time domain measurements are done with the DADiSP/32 digital signal processing software. All FF responses from the Holter tape data which are artifact-free are used for analysis.

For an in-lab study, HRV data is analyzed for 5 minutes before and for 5 minutes during the practice of FF. The time domain traces are analyzed by obtaining the overall mean heart rate for both 5-minute periods and calculating the standard deviation around that mean. FFTs of the time domain data are analyzed by dividing the power spectra into three frequency regions: VLF (0.01 to 0.05 Hz), LF (0.05 to 0.15 Hz) and HF (0.15 to 0.5 Hz). The integral of the total power in each of these regions, the total power over all regions (VLF+LF+HF), the VLF/HF ratio and the LF/(VLF+HF) ratio are calculated for each individual in the baseline and FF periods. The following criteria are used to classify the subjects into two subgroups:

Entrainment mode, characterized by a very narrow band high amplitude signal in the LF region of the HRV power spectrum, with no other significant peaks in the VLF or HF region, and a relatively harmonic signal (sine wave-like), in the time domain trace of the HRV data; and Internal coherence mode, characterized by an intentionally produced very low amplitude signal across the entire HRV power spectrum as compared to the baseline. The final discriminator of this mode is the ECG amplitude spectrum, where the first seven or so harmonics of the fundamental frequency are clearly displayed, with very few intermediate frequencies having a significant amplitude.

In general, the raw data baseline values to emotional expression values are analyzed for significance by using the Wilcoxon Signed Rank Test (T) utilizing the sum of the ranks for positive and negative differences for each group. Wilcoxon p values were taken from the table of critical values for the Wilcoxon Signed Rank Test (T). Typically, when a group is analyzed as a whole there will be no change in heart rate or heart rate standard deviation during the FF period. However, the power spectral analysis usually shows a significant decrease in the VLF/HF ratio and significant increases in LF power ($p<0.01$), HF power ($p<0.01$) and in the LF/(VLF+HF) ratio ($p<0.01$), where p is probability.

A greatly simplified overview of some of the signals and functions of the human body are illustrated in FIG. 1. This figure is not intended to be inclusive of all of the functions of the autonomic nervous system of a human, but rather provides an exemplar of those signals and functions which are currently believed to be directly related to the operation of the heart. As illustrated in FIG. 1, the brainstem 5 receives various input signals, consisting of control and status information, from throughout the body. Thus, for example, the brainstem 5 receives information relating to respiration, blood pressure, cardiac output, thermoregulation, and renin-angiotensin, as well as numerous other system inputs. Functioning as the control center of the central nervous system (CNS), the brainstem 5 continuously summarizes ($\Sigma$) all of this afferent information and synthesizes appropriate outputs to the heart 7 via either the sympathetic or parasympathetic subsystems.

Research has demonstrated that the output control signals of the sympathetic system, which is responsible for increased heart rate and blood pressure, such as in response to perceived danger, tend to be relatively low frequency (LF) rhythms. In contrast, the parasympathetic system, which operates to limit or suppress the effects of the sympathetic system, tend to be relatively high frequency (HF) signals. In general, the parasympathetic system tends to produce a quite, relaxed state whereas the sympathetic a more active, excited state. For example, on inhalation, the parasympathetic system is inhibited and the sympathetic system is more active, resulting in an increase in heart rate. In contrast, on exhalation, the parasympathetic system is active, resulting in a stronger parasympathetic signal to the heart and heart rate is decreased.

The brainstem 5 also receives afferent information from the baroreceptor network, and other receptor neurons, located throughout the heart and in the aortic arch of the heart 7, which are sensitive to stretch (pressure) and chemical changes within the heart 7. As the heart 7 beats, and its walls swell, various baroreceptors are triggered, providing signals as a function of the heart beat, where increased heart rate is generally reflected by increased baroreceptor signals.

In response to the parasympathetic and sympathetic control signals from the brainstem 5, the heart rate 7 varies. The sinus node (SN) of the heart 7 is a group of cells which act as a natural pacemaker to initiate the onset of the heart beat at a rate which is non-linearly related to the relative strengths of these autonomic control signals. It has been determined that the heart beats with a certain variability, where the time between beats is not constant but rather varies according to the shifting relative balance between the parasympathetic and sympathetic signals. A typical heart rate variability (HRV) waveform, is illustrated in FIG. 1. Note that, as illustrated, the HRV is not constant but changes with time, while still displaying a generally cyclical pattern.

Figure 2:
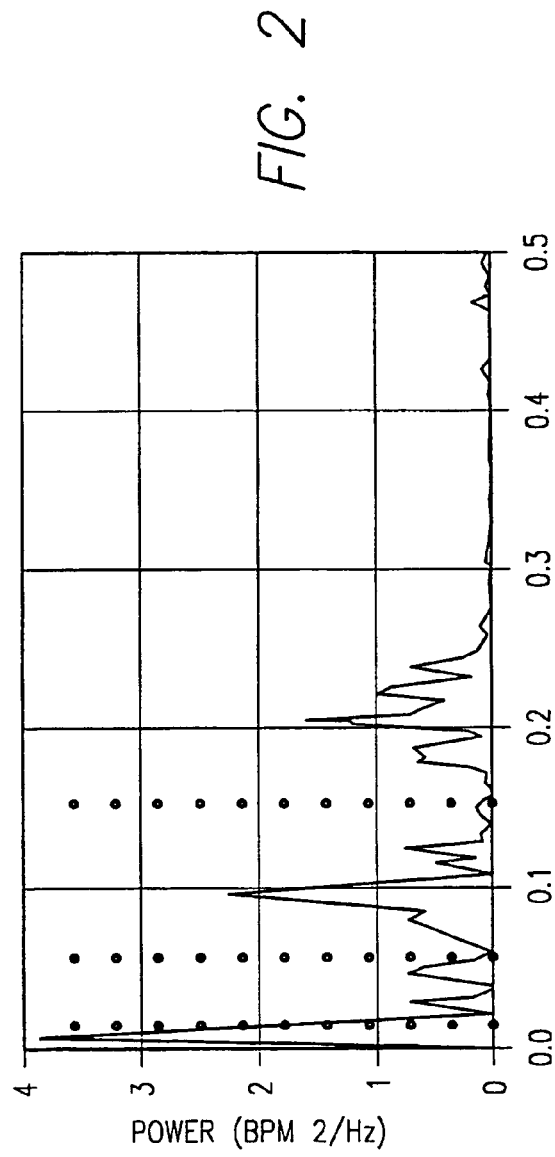
FIG. 2 illustrates a power spectrum distribution (PSD) of the HRV determined in accordance with one embodiment of the present invention.

FIG. 2 illustrates, by way of example, the transformation of an HRV waveform, most conveniently measured in the time domain, into the frequency domain. Such a transformation can be accomplished by standard digital signal processing (DSP) methods, such as the well-known fast Fourier transform (FFT). This results in a type of histogram that measures the relative amplitudes for the different frequency components (rhythmic patterns) in the time domain waveform. Fast real-time rhythms map into peaks in the high frequency portion (right side) of the spectrum, whereas slow rhythms appear on the left, low frequency side. Any given peak may be due to a single rhythmic process or to a mixture of rhythms with very similar frequencies. The latter will contribute to both the height of a peak and increase its width. In the case of heart rate analysis, different frequencies (peaks) present in the power spectrum are due to cyclic fluctuations in autonomic activity (i.e., sympathetic and parasympathetic).

Once in the frequency domain, the power spectrum distribution (PSD) is calculated using known DSP techniques, and plotted on the vertical axis with frequency on the horizontal axis. In general, the power spectrum of a waveform is a plot of the wave amplitude for each component squared, as a function of the frequency of that component. Such a plot reveals the wave power, in units of energy per hertz, present in a small frequency range as a function of frequency, f. In the present example, the units of PSD are given as a power measurement, specifically squared beats-per-minute per second ($BPM^2/Hz$, where Hertz (Hz) is frequency or cycles-per-second).

It is generally known that the mental and emotional state of a human has significant effects upon ANS activity, and, in particular, the balance between the parasympathetic and sympathetic subsystems. Such effects can be clearly seen in the HRV waveforms. We have found that, in general, agitation or fear causes disorder, whereas emotions such as appreciation or love results in increased order. The latter state has been shown to encourage coupling between respiration and the HRV as well as other oscillatory systems in the body. For purposes of the present description, we shall refer to the state in which the HRV waveform and respiratory waveform are operating at the same rate and near the 0.1 hz frequency and appear as a sine wave as entrainment. As this mode of heart function has been documented to correlate with increased balance between the sympathetic and parasympathetic branches of the nervous system it is also referred to as a state of "autonomic balance" (AB). The present invention is specifically intended to assist or facilitate a user thereof in achieving entrainment and AB at will. Once achieved, various well documented, beneficial physiological processes will be enhanced. Several embodiments of the present invention, discussed below, are specially designed to provide visual feedback to the user in a manner which tends to further strengthen and prolong the essential characteristic of entrainment and AB.

Figure 3A:
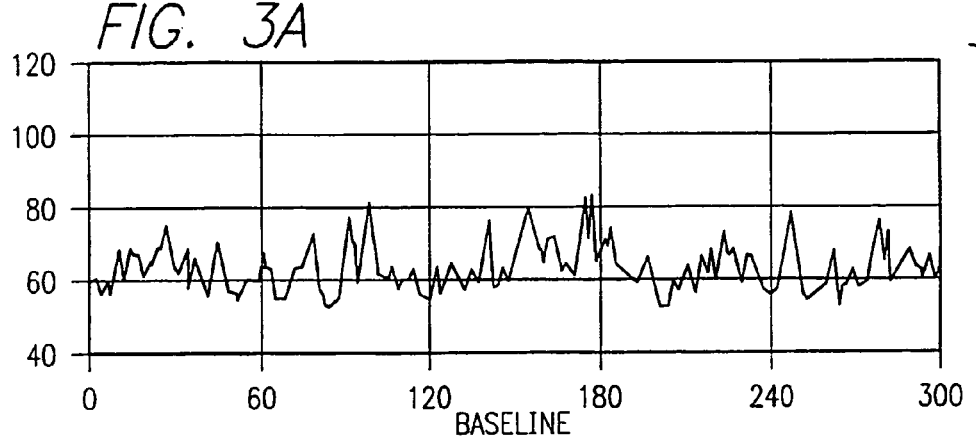
FIG. 3 illustrates, for each of four distinct ANS states, the characteristic time domain HRV and the corresponding PSD.
Figure 3A:
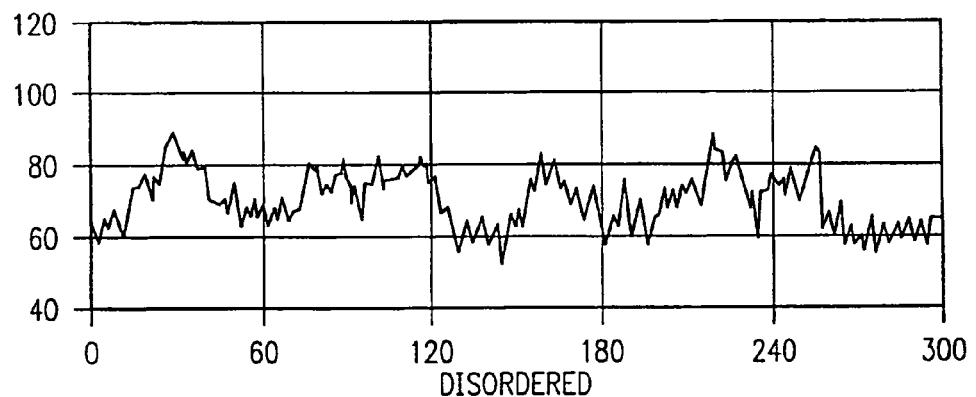
Figure 3A:
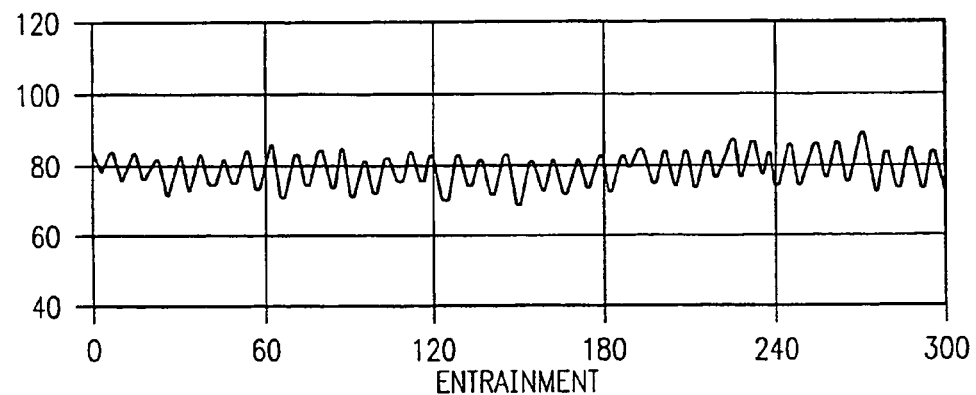
Figure 3A:
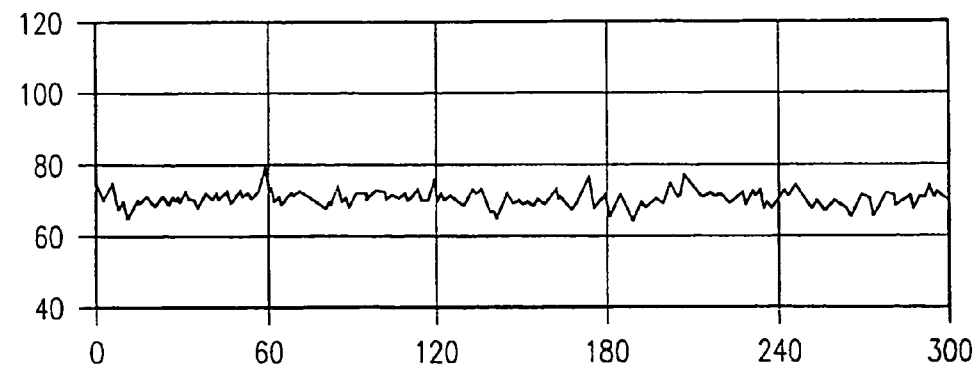
Figure 3B:
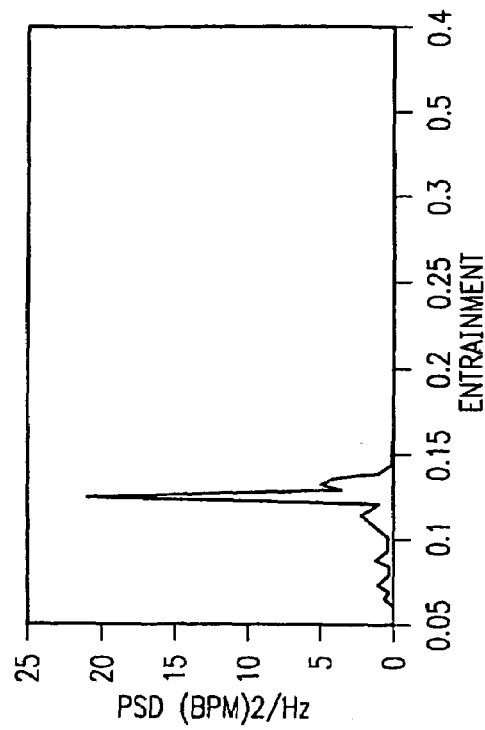
Figure 3B:
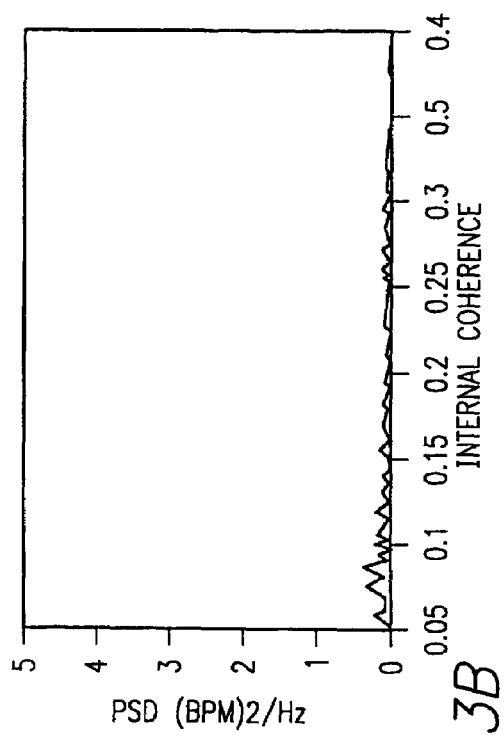
Figure 3B:
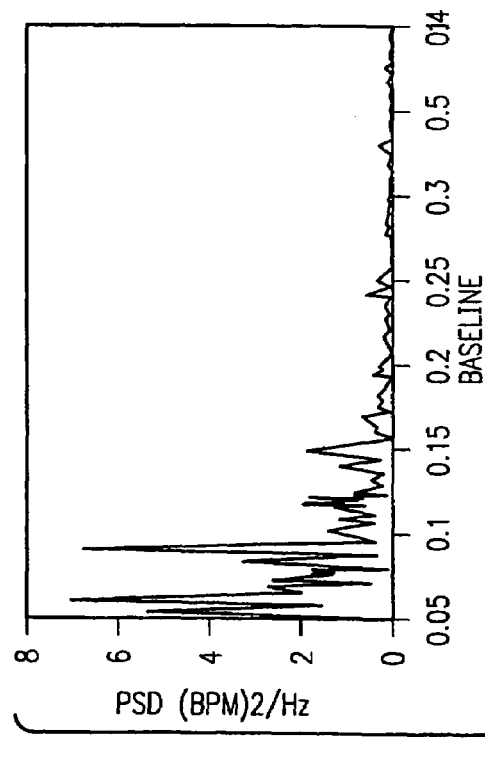
Figure 3B:
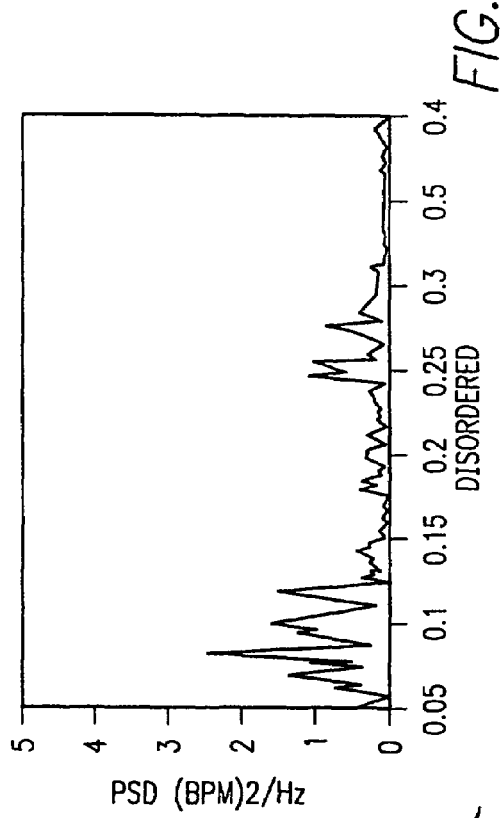

Shown in FIG. 3A is the time domain HRV of a subject in various emotional states; FIG. 3B shows the corresponding PSDs. A Baseline condition is considered to be when the subject is in a normal, resting state. A Disordered state is where the subject is feeling agitated emotions such as anger or fear. Note the more irregular nature of this waveform, clearly showing the lower frequency components contributed by the sympathetic system. In contrast, in an entrainment state, the waveform is considerably more regular and orderly. Entrainment is a condition which we have shown can be attained by following a conscious plan or protocol for effecting a positive emotional state, such as appreciation or love.

As defined herein, these terms refer to the mental and emotional state of the individual, and the graphs serve to illustrate the electrophysiological characteristics of two, qualitatively distinct "heart function modes." According to one analysis methodology, the Entrainment Mode is reached when frequency locking occurs between the HRV waveform and other biological oscillators such as respiration. Note that other correlations may be made between the HRV waveform, as well as other parameters of the heart rate and its variability, and the general state of the subject, including other physiological systems. The correspondence between HRV and the emotional and mental state of the subject is provided herein as an exemplar, as there is a strong, documented relationship. However, alternate embodiments may correlate HRV waveforms with other functions and conditions, and are not limited to those described herein as exemplars, but rather the analysis of the HRV waveform and the correlation with such conditions is achieved with the present invention. Similarly, the correspondence to emotional and mental states is not limited to those illustrated in FIGS. 3A and 3B.

Figure 4A:
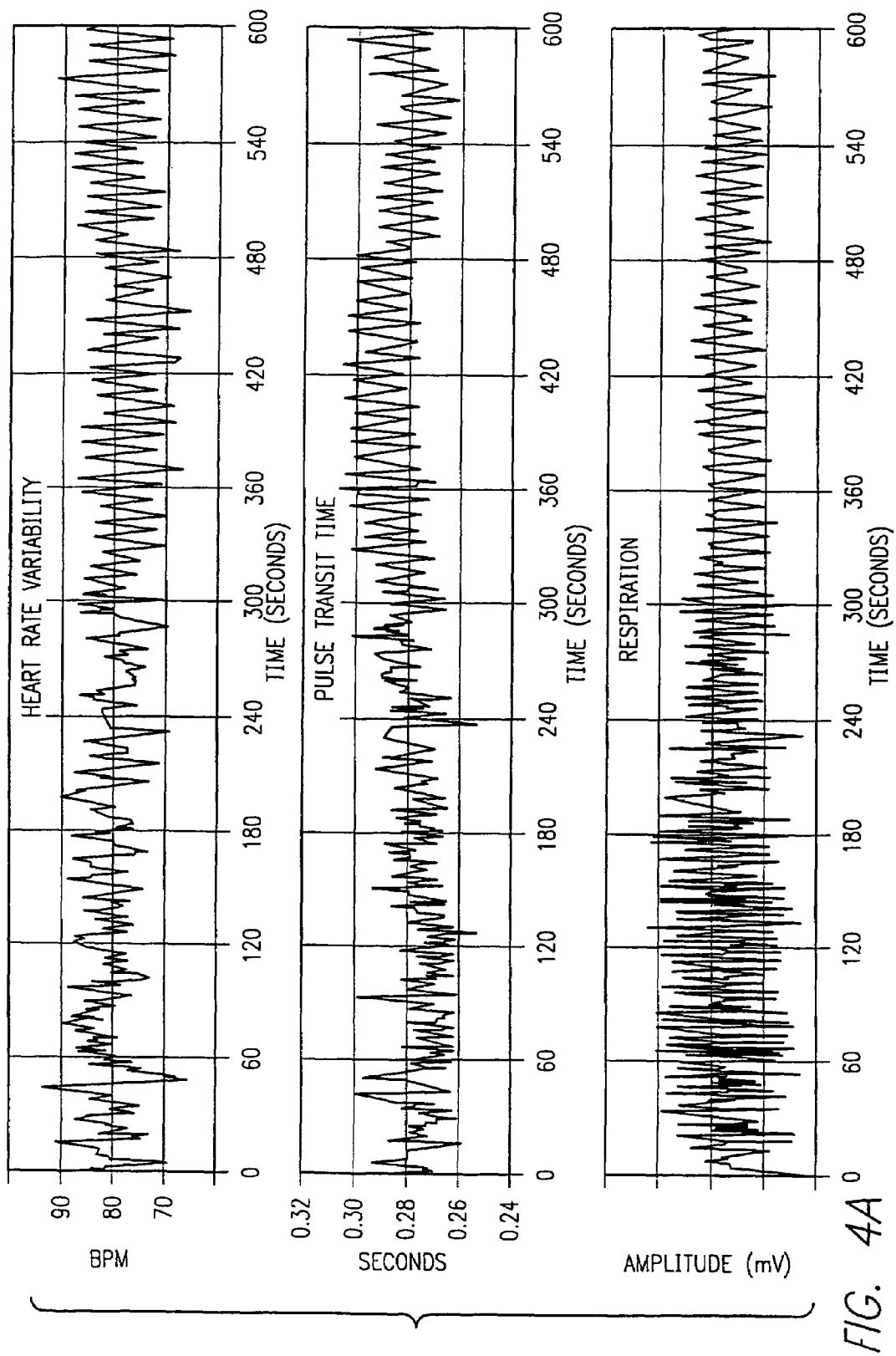
FIGS. 4A to 4C illustrate a subject's time domain HRV, pulse transit time, and respiration rates, and the corresponding PSDs, before and after the subject consciously performs an emotional self-regulation protocol specifically designed to improve the balance of the ANS.

Shown in FIG. 4A are three simultaneously recorded body responses for an individual taken before and after enacting the FF technique. The first recorded body response is HRV, displayed in beats per minute (BPM). The second recorded body response is pulse transit time (PTT), which is measured in seconds. The third recorded body response is respiration, the amplitude of which is measured in millivolts (mV). As shown in FIG. 4A, each of the recorded body responses undergo a dramatic transformation at approximately 300 seconds, the point at which the individual performs the FF technique. At that time entrainment of the HRV, PTT and respiration waveforms is achieved. Such entrainment is characteristic of AB and increased physiological coherence.

Figure 4B:
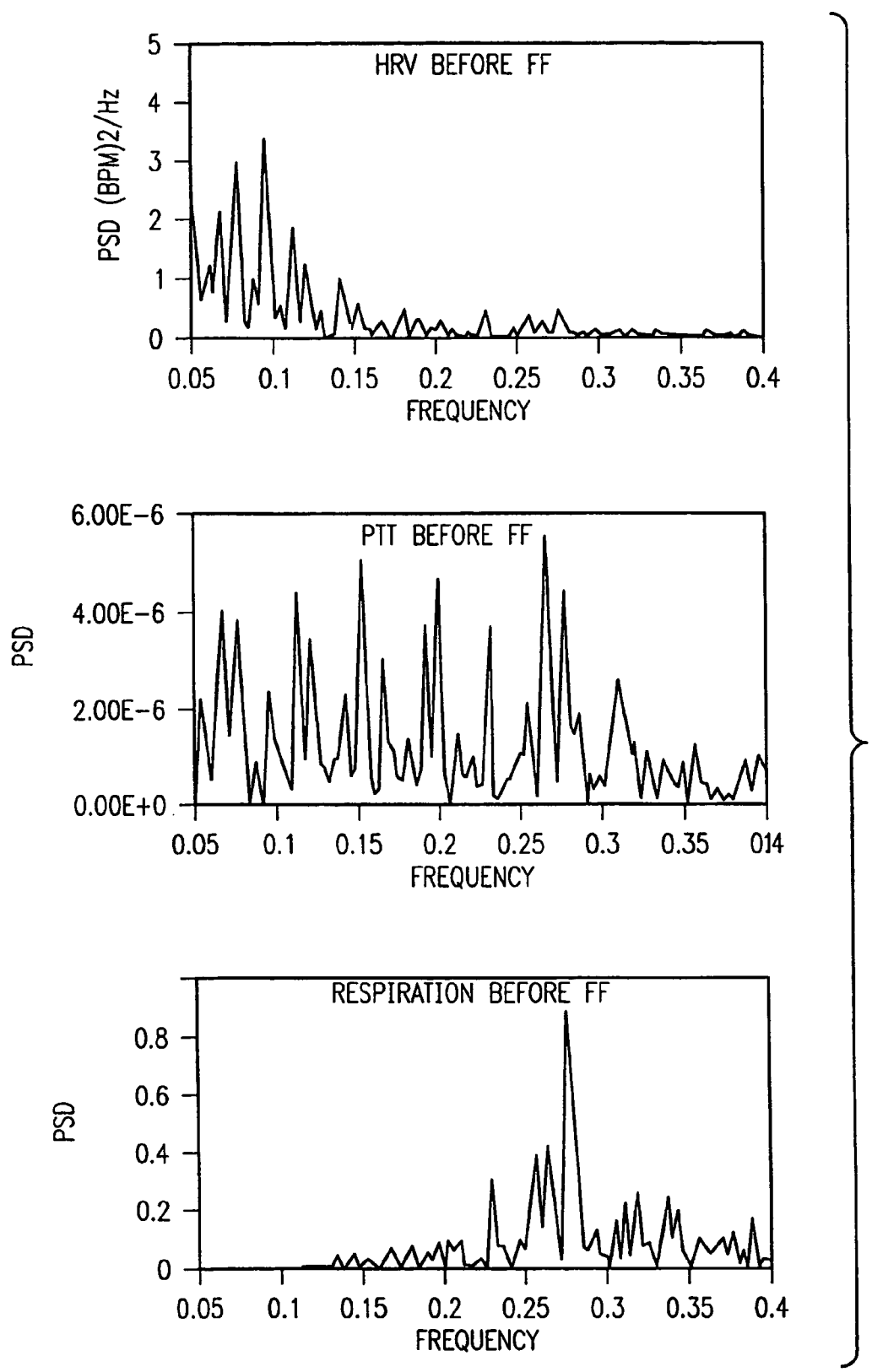
Figure 4C:
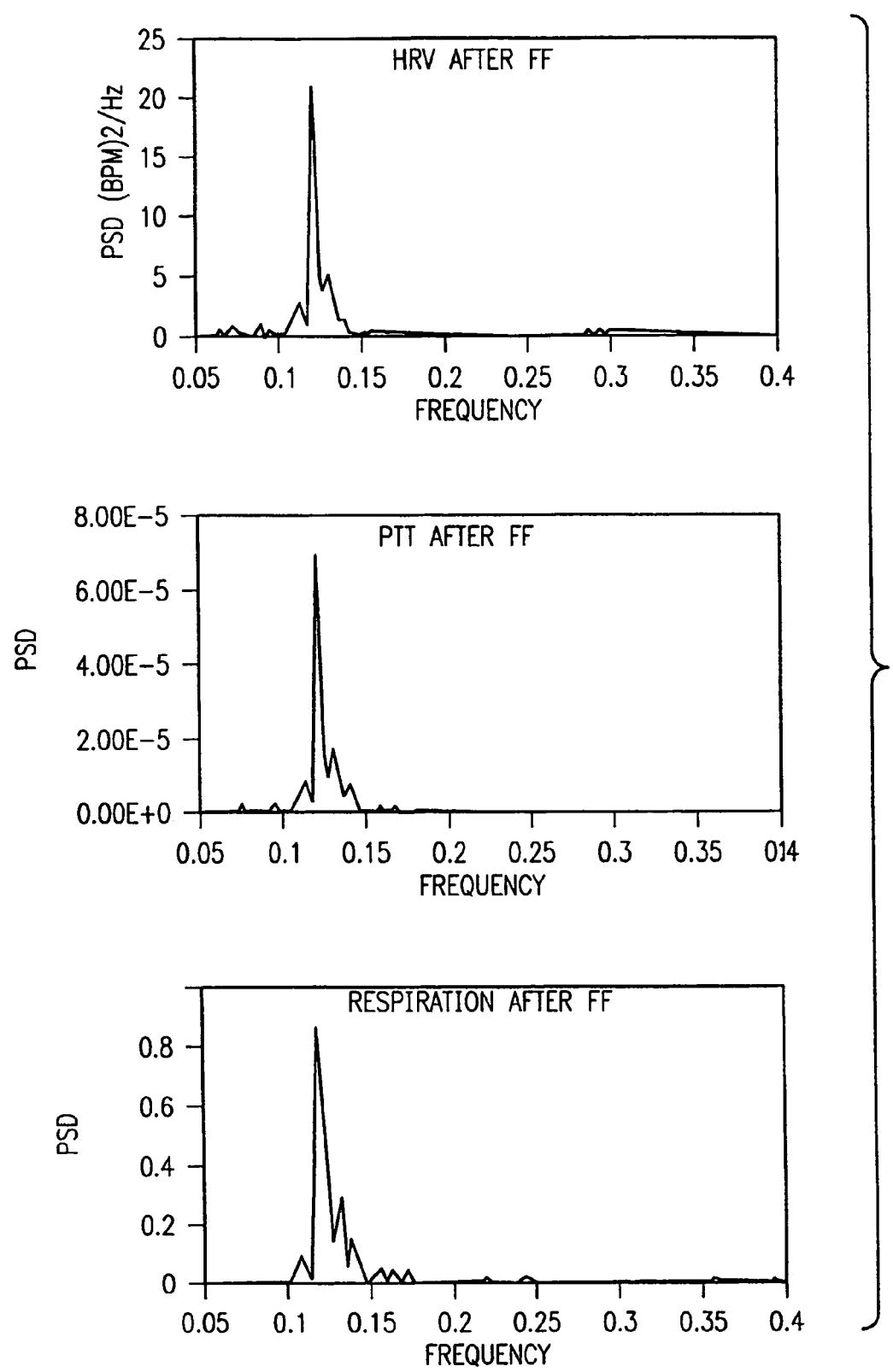

Shown in FIG. 4B are the corresponding PSD for each of the recorded body responses of FIG. 4A. Note, that the power spectra for each of the recorded body responses has a broad frequency range before performing FF. After performing FF, as illustrated in FIG. 4C, however, the power spectra for each recorded body response has a much narrower frequency range, and in each case the maximum PSD is centered between a frequency of approximately 0.1 Hz and 0.15 Hz. In addition, during entrainment, the maximum PSD for both HRV and PTT is much larger than that recorded before FF.

Figure 5:
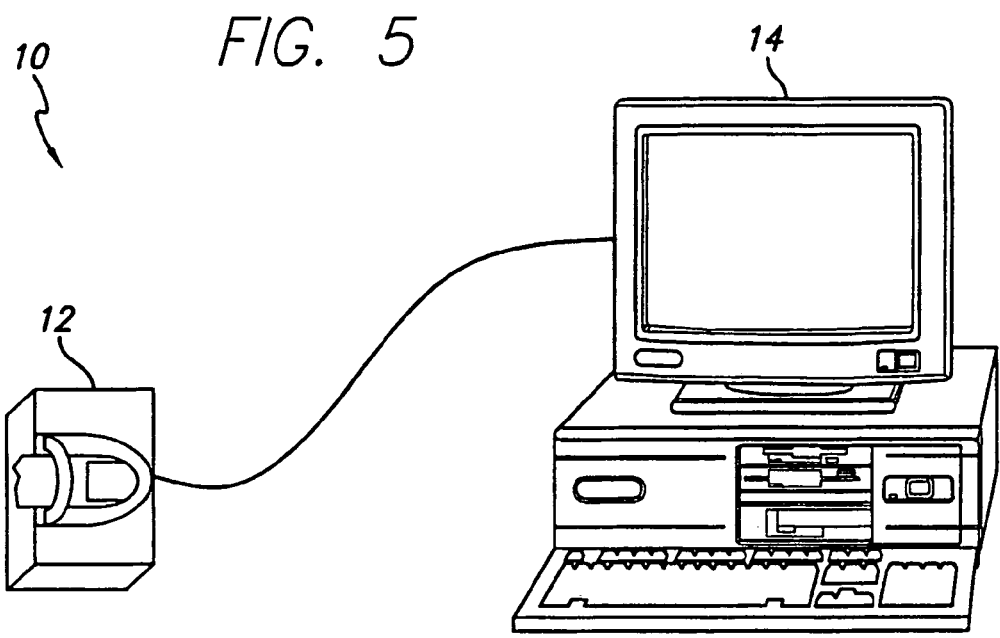
FIG. 5 illustrates an apparatus for measuring HRV and calculating the degree of entrainment, which as previously described is also an indicator of increased autonomic balance (AB) according to one embodiment of the present invention.

Shown in FIG. 5 is an entrainment apparatus 10 constructed in accordance with one embodiment of the present invention. In this particular embodiment, entrainment apparatus 10 comprises a photo plethysmographic finger sensor 12 and a computer system 14 having a monitor 15. Photo plethysmographic sensor 12 is electrically coupled to computer system 14 via coupling cable 16.

During operation, an individual's finger 18 is placed in contact with the plethysmographic sensor 12. In this particular embodiment, the sensor 12 includes a strap 20 which is placed over finger 18 to ensure proper contact between finger 18 and sensor 12. The photo plethysmographic sensor 12 detects the pulse wave produced by the heart beat of the individual, by way of finger 18, and sends this information to computer system 14. Computer system 14 collects and analyzes this heart beat data, and determines the individual's level of entrainment. A representation of the attained level of entrainment is displayed on monitor 15.

Figure 6:
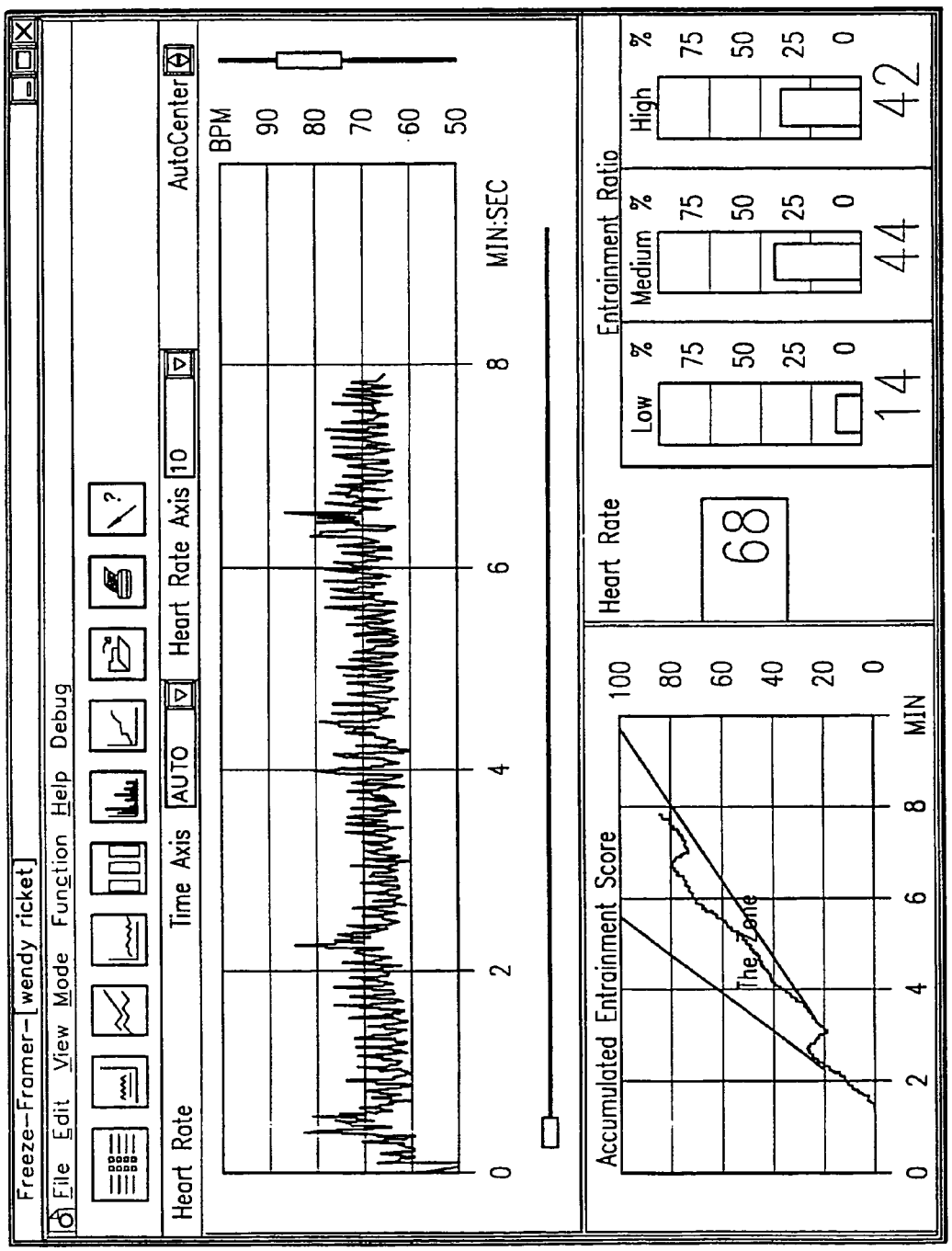
FIG. 6 illustrates one format for simultaneously displaying HRV, and the entrainment ratio, as determined in accordance with the present invention.

Shown in FIG. 6 is a display output 22 produced by entrainment apparatus 10 in accordance with one embodiment of the present invention. In this particular embodiment, the individual's heart rate, measured in beats per minute (BPM), is graphically displayed for a selected time period. The individual's accumulated entrainment score for this same time period is graphically displayed in reference to the calculated entrainment zone. In addition, the individual's entrainment ratio and average heart rate are also graphically displayed for this same time period.

FIGS. 7A–7E illustrate a method of calculating an entrainment parameter (EP) according to the preferred embodiment of the present invention. In general, the method involves monitoring the beat-to-beat changes in heart rate, calculating the EP, and presenting a representation of the categorization of the calculated EP. The method begins at start block 30. The process is initialized at step 32, where HRV data is obtained and processed in preparation for the next step. At step 34 an entrainment parameter (EP) and score are calculated. The entrainment parameter is determined by the power distribution of the HRV processed data, and the score is a historical indication of the EP. The EP and score are then presented at step 36, which may involve providing this information to a display terminal. The process continues to decision diamond 38, to determine if the process is to terminate or end. If the process is to end, processing continues to step 40 where the process is terminated. If the process is not to end, process flow returns to block 34.

Figure 7A:
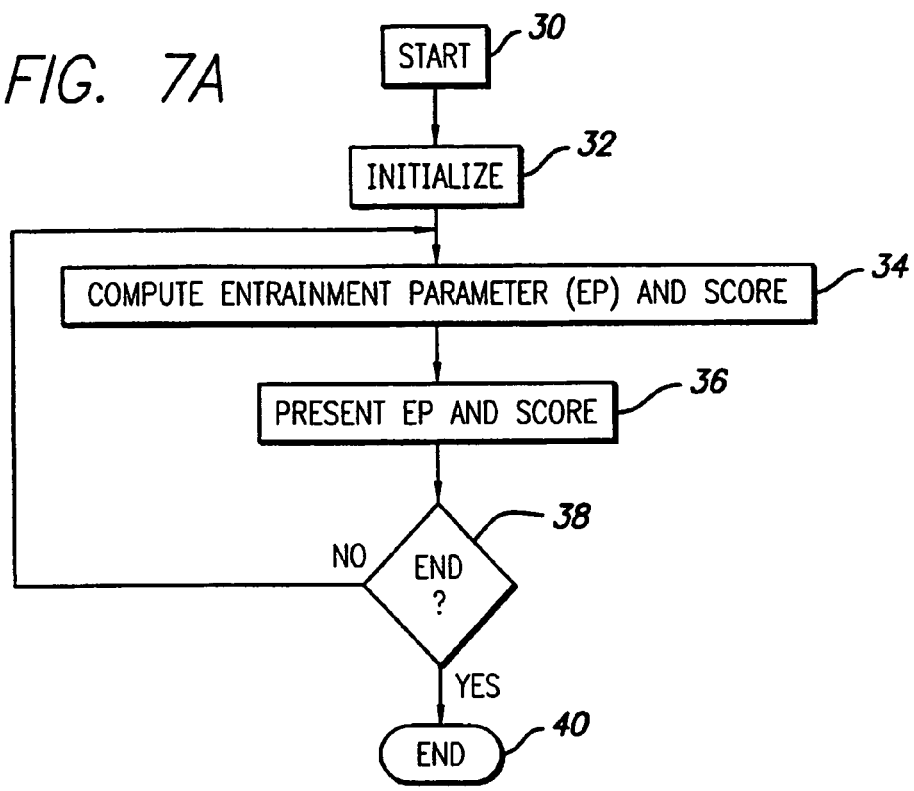
FIGS. 7A–7E illustrate in flow chart form a process for calculating AB in accordance with the present invention.
Figure 7D:
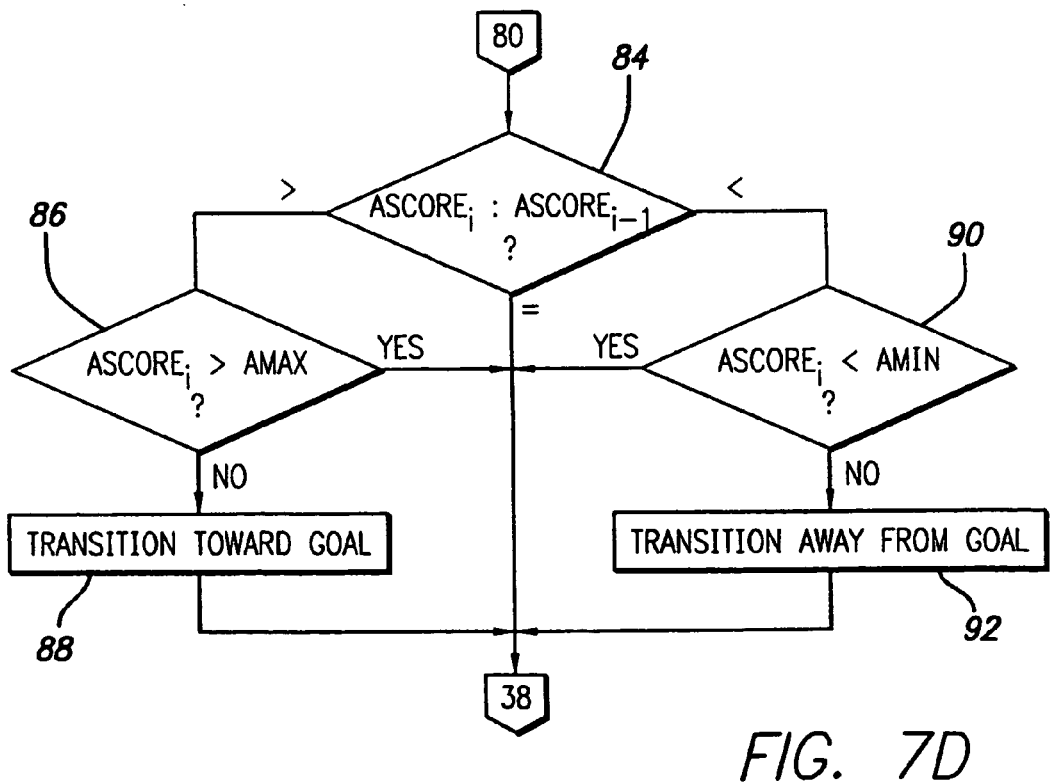
Figure 7B:
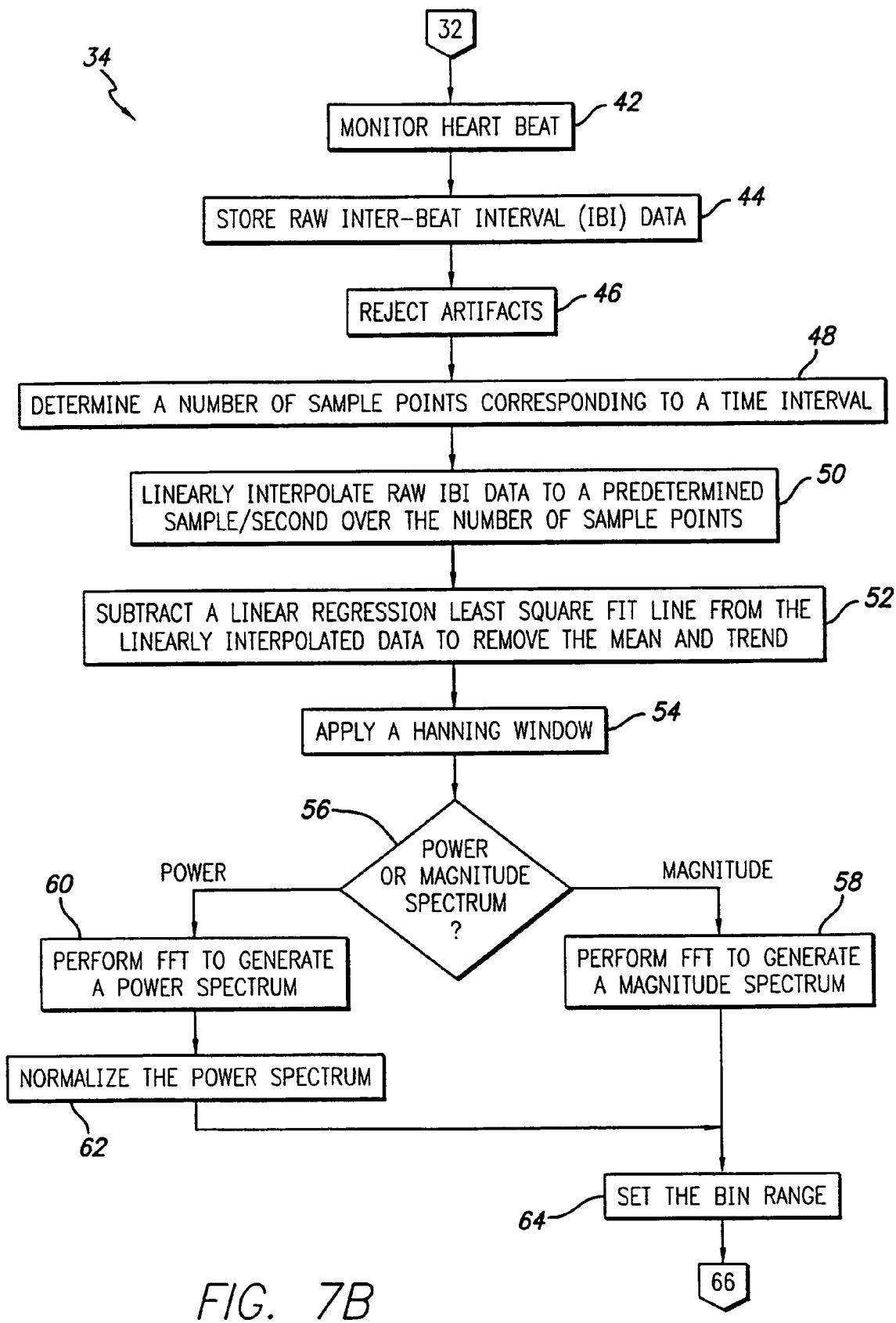
Figure 7C:
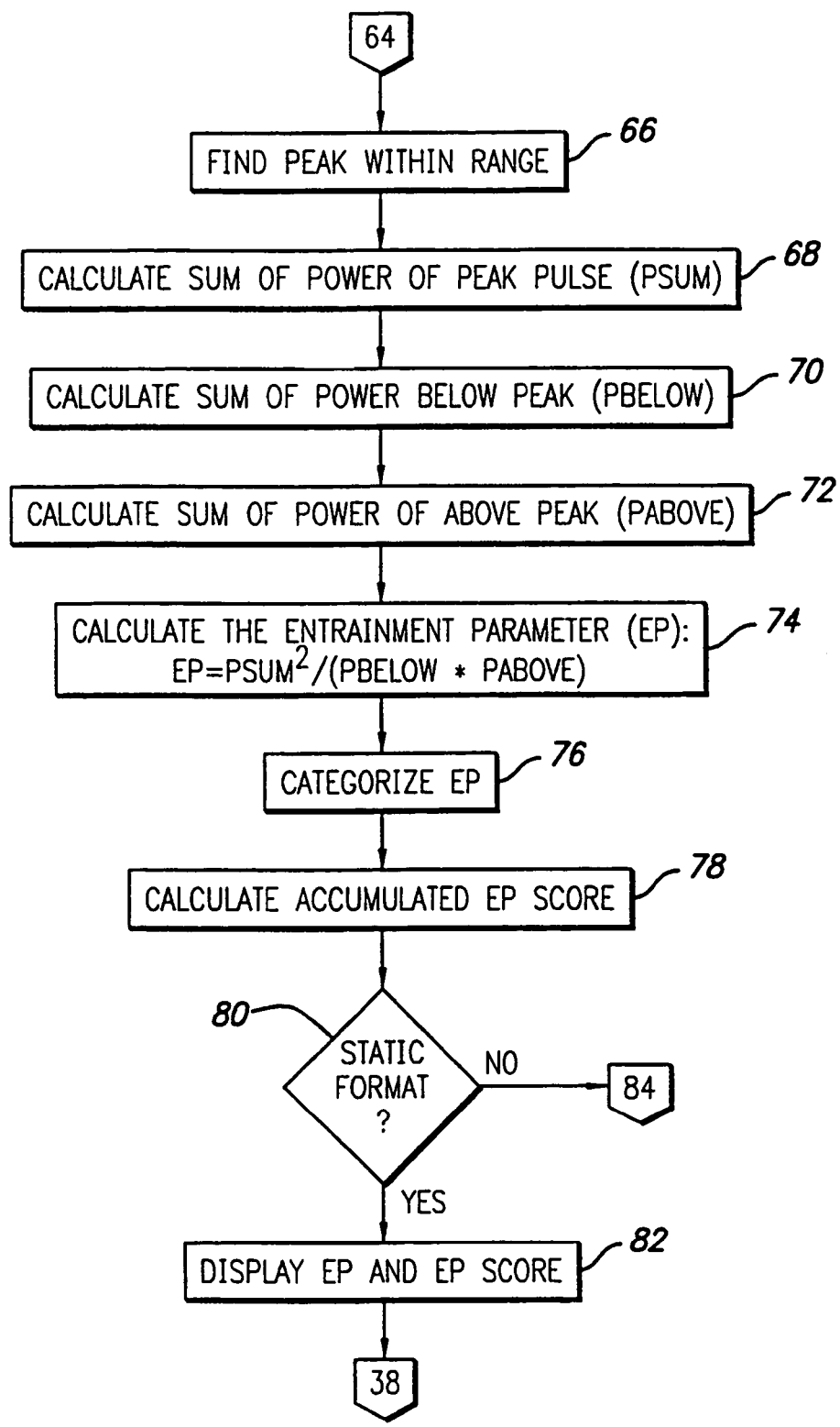
Figure 7E:
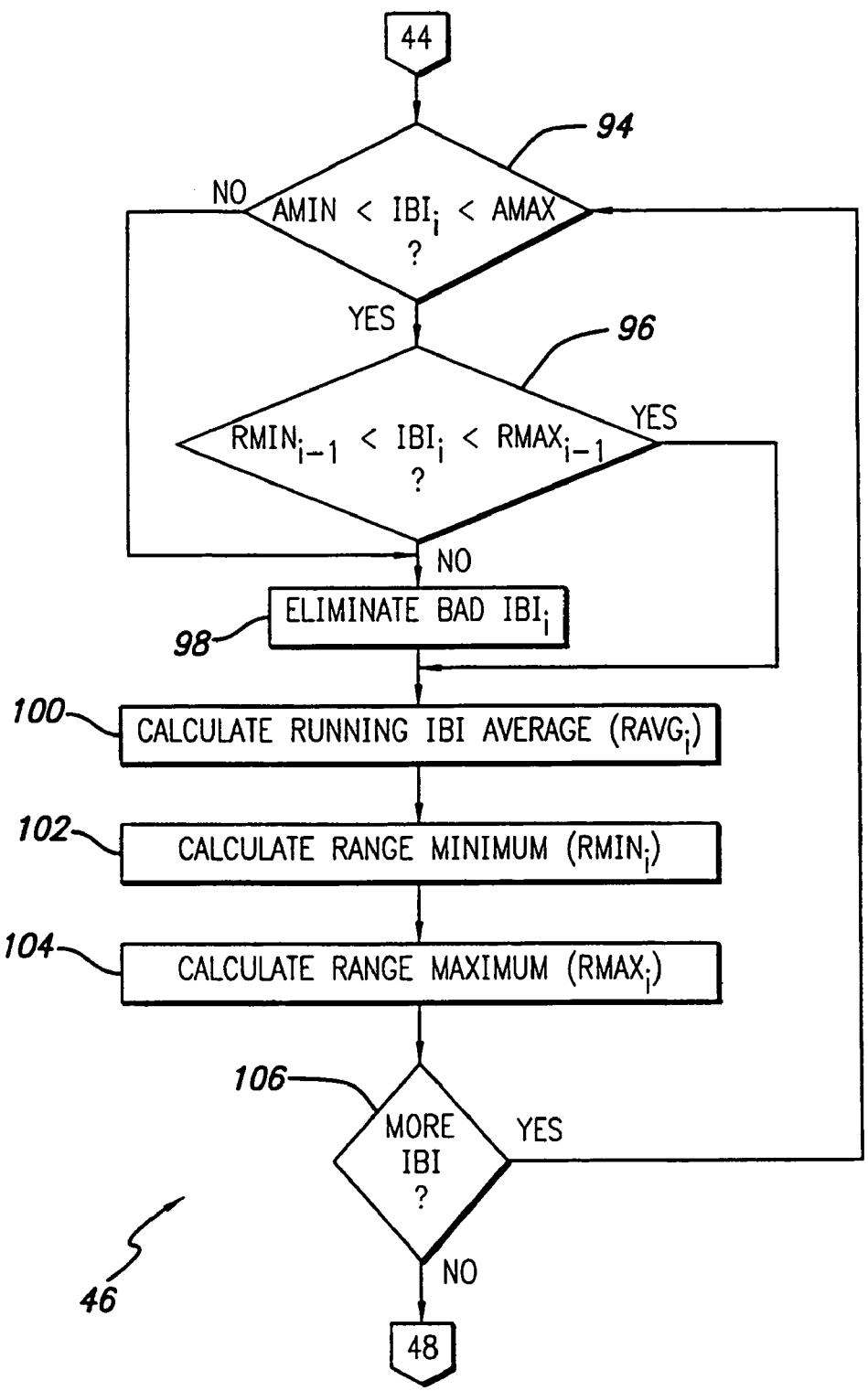

The process is further detailed in FIG. 7B, where the heart beat is monitored at step 42. This may involve using electrical sensing apparatus, such as an electrocardiograph (ECG), light sensing apparatus, such as the photo plethysmographic sensor 12, or any other apparatus or means whereby each heart beat can be ascertained substantially in real time. For example, at regular time intervals, say 100 times per second, the output of sensor 12 is sampled and digitized using a conventional analog-to-digital (A/D) converter (not shown). At step 44, the raw samples are stored. This raw data is basically a record of each heart beat and the relative time of its occurrence. The stored raw data can be thought of as comprising inter-beat-interval (IBI) information, from which the time interval between beats can be determined. It is the IBI variation which is generally referred to as "heart rate variability" or simply HRV.

Note that in monitoring the heart beat, artifacts, such as noise and/or misreads, may have a tendency to disturb the process. An optional step is provided at block 46 where the artifacts and other artificially introduced noise are rejected. This may be done using a conventional DSP artifact rejection technique. Block 46 is further detailed in FIG. 7E, starting $$Ravg_{i-1}(1-Pmin)$$

at decision diamond 94. Here the current IBI, referred to as $IBI_i$ is compared to an absolute minimum interval between beats (Amin) and to an absolute maximum interval between beats (Amax). Amin and Amax are reflect the actual range within which the human heart beat falls. For example, Amax and Amin indicate that IBI is either too long and too short respectively, and IBI does not normally occur at that value; thus these conditions are used to detect artifacts which are not accurate data. If $IBI_i$ falls between these two extremes processing continues to step 96. If $IBI_i$ does not fall within this range, no further check is made and processing jumps to step 98 for elimination of bad $IBI_i$ data. Note that a running average (Ravg) is calculated for IBI values. A range of Ravg values is determined for each $IBI_i$ and is then used to verify then next value, $IBI_{i+1}$. The range of Ravg values is determined as a percentage of the IBI value. For evaluation of $IBI_i$ the range of Ravg values for $IBI_{i-1}$ is used. In one embodiment, the range is defined between $Rmin_{i-1}$ and $Rmax_{i-1}$, where $Rmin_{i-1}$ is $Ravg_{i-1}$ −30% and $Rmax_{i-1}$ is $Ravg_{i-1}$+30%. $IBI_i$ falls within this range if it satisfies the following relationship:

$$IBI_i \epsilon [Ravg_{i-1}(1-Pmin), Ravg_{i-1}(1+Pmax)]$$

Continuing at step 96, if $IBI_i$ is within this range, processing jumps to step 100. If $IBI_i$ is not within this range, processing continues to step 98 where $IBI_i$ is eliminated as bad data. In a preferred embodiment, if too many errors are encountered, calculation is frozen until sufficient good data is received to warrant continuing. Sufficient good data is indicated by the following relationship:

$$Amin < \forall \epsilon [IBI_j, IBI_k] < Amax$$

wherein IBI includes values $IBI_j, \ldots IBI_k$. At step 100 the running average of $IBI_i$ is calculated as $Ravg_i$. At step 102 the minimum range of Ravg for $IBI_i$ is calculated as $Rmin_i$. At step 104 the maximum range of Ravg for $IBI_i$ is calculated as $Rmax_i$. These values will be used to verify the next IBI value, $IBI_{i+1}$. Processing then continues to decision diamond 106 to determine if further IBI processing is to be done, and if so processing returns to decision diamond 94. If not, processing continues to step 48.

At step 48, a conveniently sized segment of the raw data samples, say 64 seconds, is selected, and then linearly interpolated using standard DSP techniques, at step 50. To facilitate discrimination, the raw IBI data points have been scaled by 1000, i.e., converted to milliseconds. The HRV graph shown in FIG. 8A illustrates a representative set of scaled IBI data and the linearly interpolated data points, where the IBI data points are indicated by a black dot and the interpolated data points are indicated by "x."

At step 52, the selected segment of HRV data is demeaned and detrended by subtracting a linear regression least squared fit line (a common DSP technique) to center the waveform with respect to the vertical axis, and to remove any tendency of the waveform to slowly decrease or increase. As illustrated in FIG. 8B, the HRV segment exhibits a decreasing trend over time, as can be seen from the superimposed linear regression line.

As will be clear to those skilled in this art, the segmentation process performed in step 48 has the undesirable side effect of convolving the HRV data with a square wave, and thus tends to introduce noise at the boundaries between each segment. For example, where the number of data points in each segment is 128, there will be significant noise introduced between sample 128 and 129. A well known DSP technique, called Hanning windowing, effectively weights the center data points of the segment more heavily than those at the edges to reduce the effects of this noise. As used in the present embodiment, the Hanning window equation uses a cosine taper as follows:

$$W(n)=0.5-0.5\cos(2\pi/N^*n)$$

where N is the total number of data points in the segment, and n=[1,N−1]. At step 54, such a Hanning window is applied to the detrended data to eliminate the segmentation noise. As illustrated in FIG. 8C, the resultant HRV waveform is zero-referenced and exhibits no trend. It should be recognized that various other alternate methods or techniques can be employed to remove such noise as may have been introduced as artifacts of the recording, interpolating or segmentation processes.

At step 56, a user-established system control variable is examined to determine what type of spectrum analysis needs to be performed. If a magnitude spectrum is selected, an FFT is performed at step 58 to generate a magnitude spectrum. On the other hand, if a power spectrum is selected, the PSD of the detrended data is calculated, in step 60, using a standard FFT. This PSD is then normalized, at step 62, by dividing by the length of the segment in seconds (see, step 33). For example, if the number of data points was selected to be 128 points, the PSD is divided by 64, the duration of the segment, i.e., 64 seconds. This makes the units of power $ms^2/Hz$. Note that such a normalization process is not necessary if the magnitude spectrum is used.

Figure 8D:
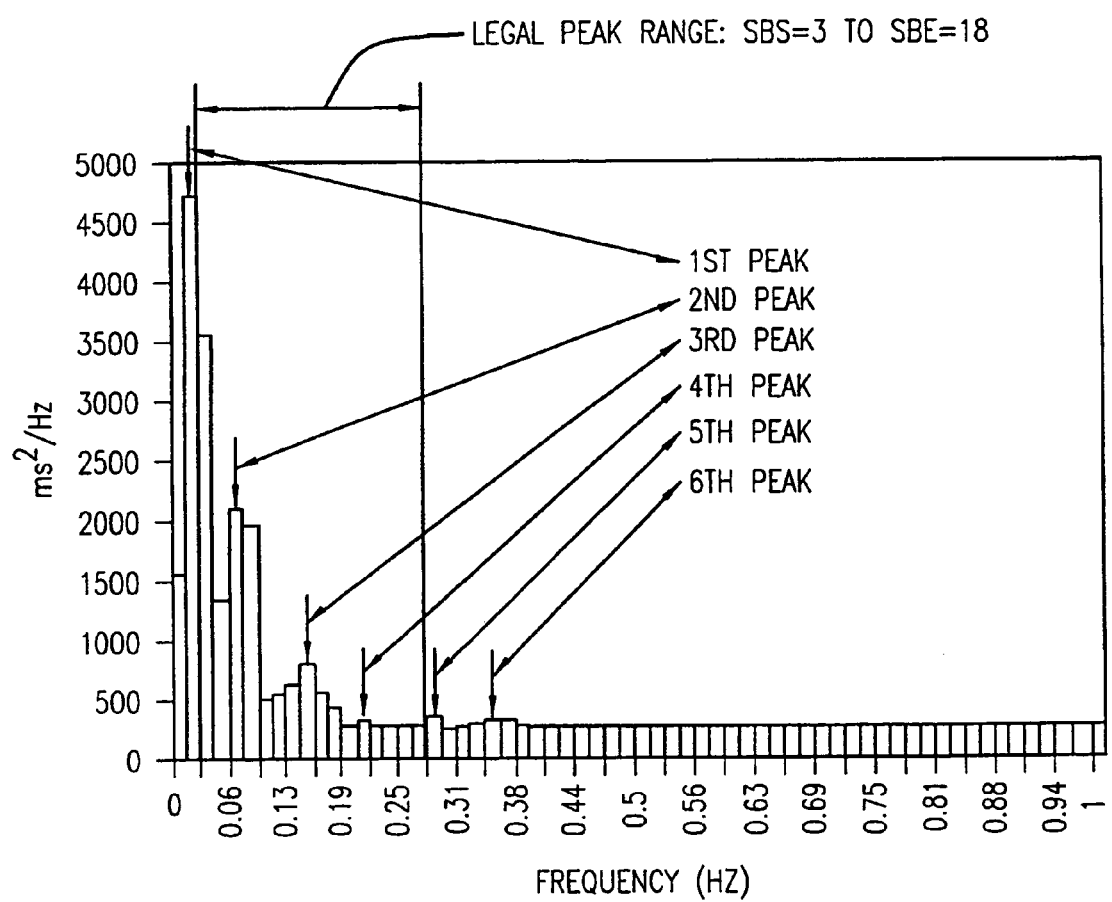

The result after step 58 or 62 is illustrated in FIG. 8D, where the horizontal axis represents frequency (Hz) and the vertical axis represents power ($ms^2/Hz$). Note that HRV is portrayed in the form of a bar chart, wherein each bar represents the power contained in the HRV signal within a respective, narrow band of frequencies comprising a "bin," as illustrated in FIG. 8D. For convenience of reference, the bins are logically numbered sequentially, starting with bin 1 on the far left, and continuing to bin 64 on the far right, where each bin corresponds to a frequency. At step 64, a pair of user-selected system control variables is examined to select the range of bins from which the highest local peak will be selected. As it can be anticipated that the desired peak will be within a certain frequency range, it is neither necessary nor reasonable to consider the entire PSD. According to one embodiment, the starting search bin is selected by a variable "search bin start" (SBS), while the ending search bin is selected by a variable "search bin end" (SBE). For the example illustrated in FIG. 8D, the SBS is equal to 3 and the SBE is equal to 18, comprising the search range of bins 3, 4, 5, . . . , 18.

At step 66 (FIG. 7C), a search is made, within the bin range selected in step 64, for all local peaks in the HRV spectrum, each being represented by the single bin having the highest power level, i.e., the bin underneath the respective peak. Next, the bin representing the highest peak within the bin range is selected. In the example shown in FIG. 8D, there are three peaks within the bin range of bin 3 to bin 18. The highest peak is located at bin 5. Note that the first, and absolute largest, peak is represented by bin 2, so bin 3 is not considered to represent a peak.

Once the highest peak within the selected bin range has been determined, an entrainment parameter (EP) is calculated to indicate the energy of the wave in the entrainment area in relation to the total energy in the PSD. To calculate the EP, at step 66, the "width" of the peak is determined from a pair of user-selected variables: P1, which defines the number of bins to the left of the peak bin, and P2, which defines the number of bins to the right of the peak bin. Note that P1 and P2 may be different if an asymmetric distribution is desired. The total energy of the peak, Psum, is then calculated as the sum of the power values of all bins in the range [(Peak−P1), (Peak+P2)] at step 68.

Figure 8E:
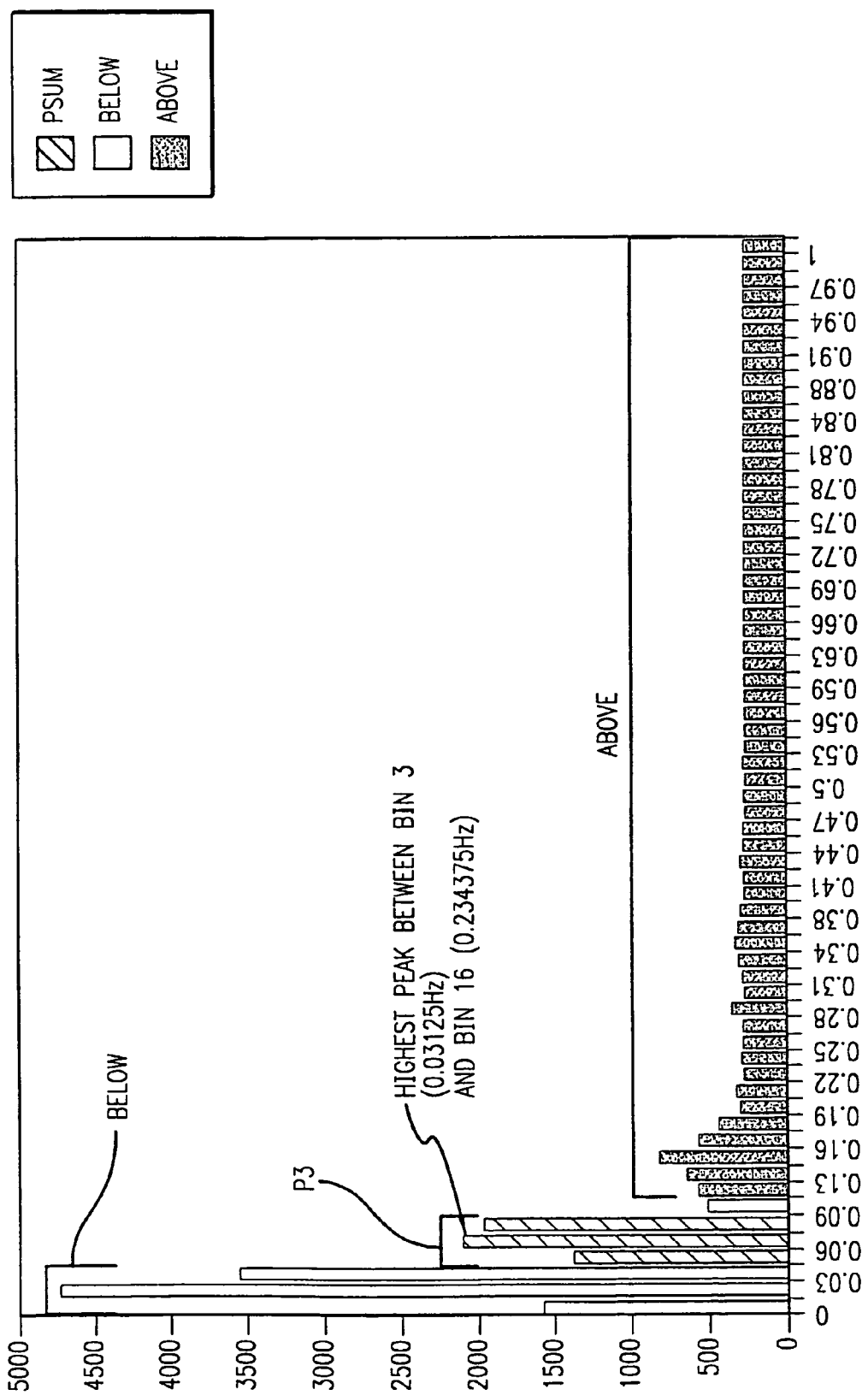

Next, at step 70, the total power below the peak pulse (Pbelow) is calculated. The relevant range is determined by a pair of user-selected variables: B1 and B2. The value of Pbelow is a summation of the power values of all bins in the range [B1, B2]. Similarly, at step 72, the total power above the peak (Pabove) is calculated, within a relevant range determined by a pair of user-selected variables: A1 and A2. The value of Pabove is a summation of the power values of all bins in the range [A1, A2]. This is clearly illustrated in FIG. 8E. Finally, at step 74, EP is calculated according to the following equation:

$$EP=(P\text{sum}/P\text{below})*(P\text{sum}/P\text{above}).$$

At step 76, the EP value is then "scored" according to a plurality of user-selected entrainment level thresholds. For example, three stages of entrainment can be conveniently defined using only two variables, NLT1 and NLT2, each of which represents a respective value of EP. In such an embodiment, for EP below NLT1, the subject may be considered as not having achieved significant entrainment, and is given a score of "0". For EP above NLT1 and below NLT2, the subject is considered to have achieved mild entrainment, and is given a score of "1". For EP above NLT2, the subject is considered to have achieved full entrainment, and is given a score of "2". Of course, other criteria may be used to determine achieved entrainment level.

Figure 8F:
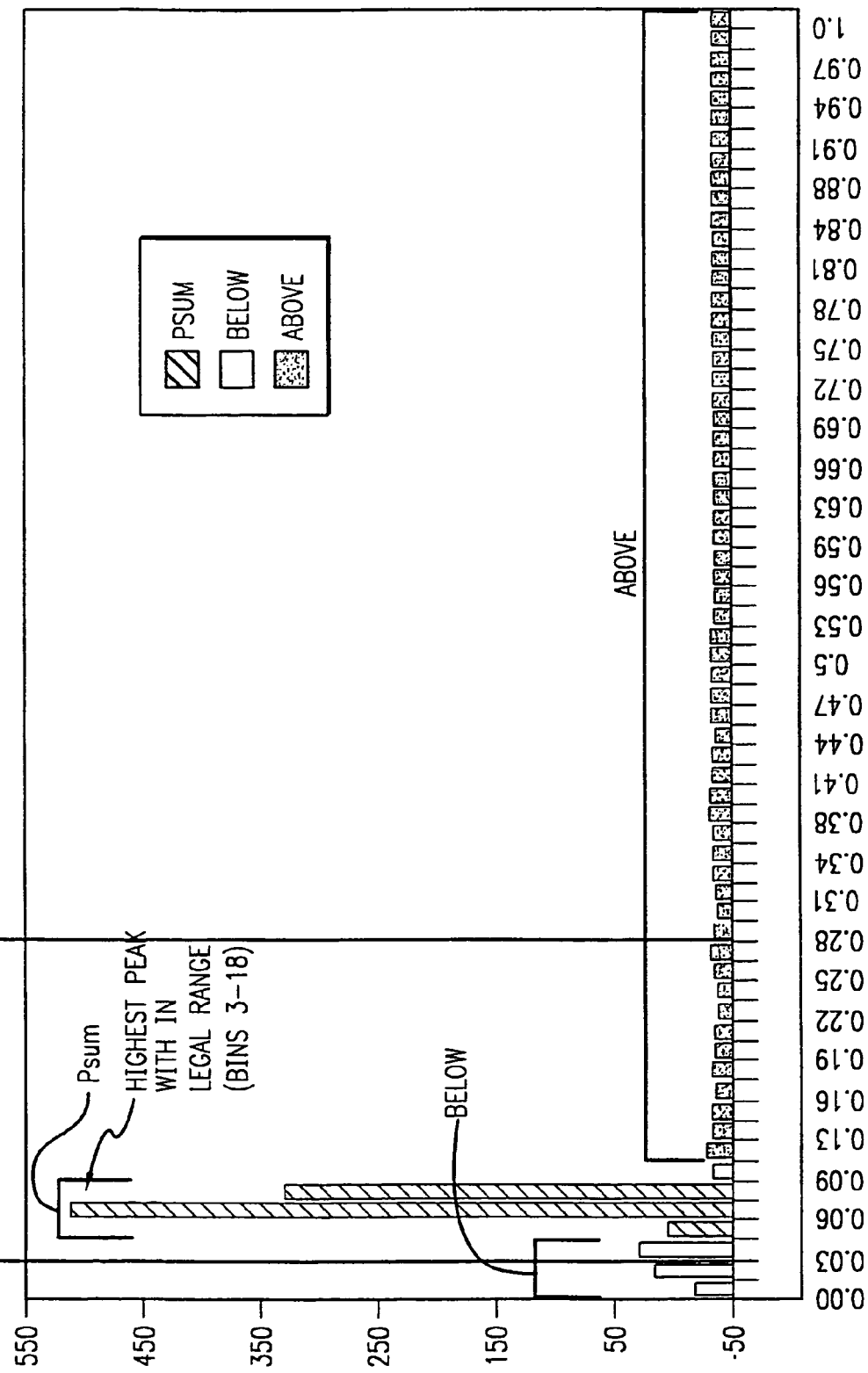

In general, maximum entrainment is reached when the peak pulse contains a very large portion of the total power. A particularly high EP is illustrated in FIG. 8F, where Psum is great compared to both Pbelow and Pabove. This indicates that most of the power is concentrated at this small group of frequencies. Thus, EP tends to emphasize the condition wherein the majority of the power is concentrated within a selected, relatively narrow range of frequency bins. On the other hand, it is certainly possible to devise alternate calculations which will reflect concentration of significant levels of power distributed over a broader range of frequency bins.

At step 78, the most recently calculated score is recorded and an accumulated score is calculated based on prior, historical scores, referred to as accumulated scores. At step 36, the actual EP result and accumulated scores are prepared for presentation to the user as a system output. This preparation involves steps such as 76 and 78.

At decision step 80, it is determined if the user desires this information to be simply output on a status screen of the computer, in a presentation format such as that shown by way of example in FIG. 6. In the preferred embodiment of the present invention, the user can elect to have this information control a game, such as the balloon game shown in FIG. 10. If the user so selects, at decision step 80, EP is compared to a various threshold levels and assigned an EP score accordingly.

According to one embodiment, EP is assigned a score selected from the set of {0, 1, 2}. The score values have the following significance:

| EP Score | EP value | Entrainment |
|---|---|---|
| 0 | EP < level1 | Low |
| 1 | level1 < EP ≤ level2 | Medium |
| 2 | level2 < EP | High |

According to one embodiment, level1 is set to 0.9, and level2 is set to 7.0, to provide a convenient distribution. In a computer program implementing this embodiment, these levels are provided as floating point values. Alternate embodiments may use additional levels, or may use two levels.

If the user selects a nonstatic format, processing continues to step 84 of FIG. 7D, where the accumulated score, "Ascore," is calculated based on the historical information of the EP and EP score values. Ascore is then calculated based on the score value, and the previous score value (prescore). This calculation is performed according to the following scheme:

| EP Score | EP Prescore | Ascore(i) |
|---|---|---|
| 2 | 0 | Ascore(i − 1) + 1 |
| 1 | 0 | Ascore(i − 1) + 1 |
| 0 | 0 | Ascore(i − 1) − 2 |
| 2 | 1 | Ascore(i − 1) + 1 |
| 1 | 1 | Ascore(i − 1) + 1 |
| 0 | 1 | Ascore(i − 1) − 1 |
| 2 | 2 | Ascore(i − 1) + 2 |
| 1 | 2 | Ascore(i − 1) + 1 |
| 0 | 2 | Ascore(i − 1) − 2 |

According to one embodiment, Ascore has values in the range of {0, 1, 2, . . . 100}, however alternate embodiments may use an alternate range of values. The above scheme provides scaled response to the EP, where Ascore slowly increases while remaining in medium entrainment, but quickly increases while remaining in high entrainment. Similarly, this scheme provides a quick decrease while remaining in the low entrainment.

Ascore information may be then be used to provide a graphical display. One embodiment, illustrated in FIG. 7D begins at decision diamond 84 to determine the value of $Ascore_i$ with respect to $Ascore_{i-1}$. $Ascore_i$ is the current calculated value of Ascore, and $Ascore_{i-1}$ is the previous calculated value of Ascore.

If $Ascore_i$ is equal to $Ascore_{i-1}$, processing returns to step 38 without effecting any change in the graphical display. Note that alternate embodiments may include additional steps which provide this information to the display. If $Ascore_i$ is greater than $Ascore_{i-1}$, processing continues to decision diamond 86 to determine if $Ascore_i$ has reached an $Ascore_{max}$ value. According to one embodiment, $Ascore_{max}$ is equal to 100. If $Ascore_i$ is not greater than $Ascore_{max}$, processing continues to step 88. At step 88 a graphical element transitions toward a goal. In one embodiment, the graphical element is a balloon, and the transition is to rise vertically into the air. In an alternate embodiment, the graphical element is a rainbow, and the rainbow begins to fill in colors to reach a pot of gold. Once the rainbow reaches the pot of gold, the pot begins to fill with coins and may overspill. In still another embodiment, a peaceful scene is slowly filled in with color and detail. Alternate embodiments may include other scenes, icons, or images, and may include obstacles to be overcome or various stages to be reached. Processing then returns to step 38.

Continuing with FIG. 7D, If $Ascore_i$ is greater than $Ascore_{max}$, processing returns to step 38 without effecting any change in the graphical display. Note that alternate embodiments may include additional steps which provide this information to the display.

Returning to step 84 of FIG. 7D, if $Ascore_i$ is less than $Ascore_{i-1}$, processing continues to decision diamond 90 to determine if $Ascore_i$ has reached an $Ascore_{min}$ value. According to one embodiment, $Ascore_{min}$ is equal to 0. If $Ascore_i$ is not less than $Ascore_{min}$, processing continues to step 92. At step 92 a graphical element transitions away from a goal. In one embodiment where the graphical element is a balloon, the transition is to lower vertically toward the ground. In an alternate embodiment where the graphical element is a rainbow, the rainbow begins to lose colors and separate from a pot of gold. If the pot of gold includes gold coins, these coins are removed. In still another embodiment where a peaceful scene is displayed, color and detail are slowly removed from the display. Alternate embodiments may include other scenes, icons, or images, and may include obstacles to be overcome or various stages to be reached. Processing then returns to step 38.

At decision diamond 90, if $Ascore_i$ is less than $Ascore_{min}$, processing continues to step 38 without effecting any change in the graphical display. Note that alternate embodiments may include additional steps which provide this information to the display.

Figure 10:
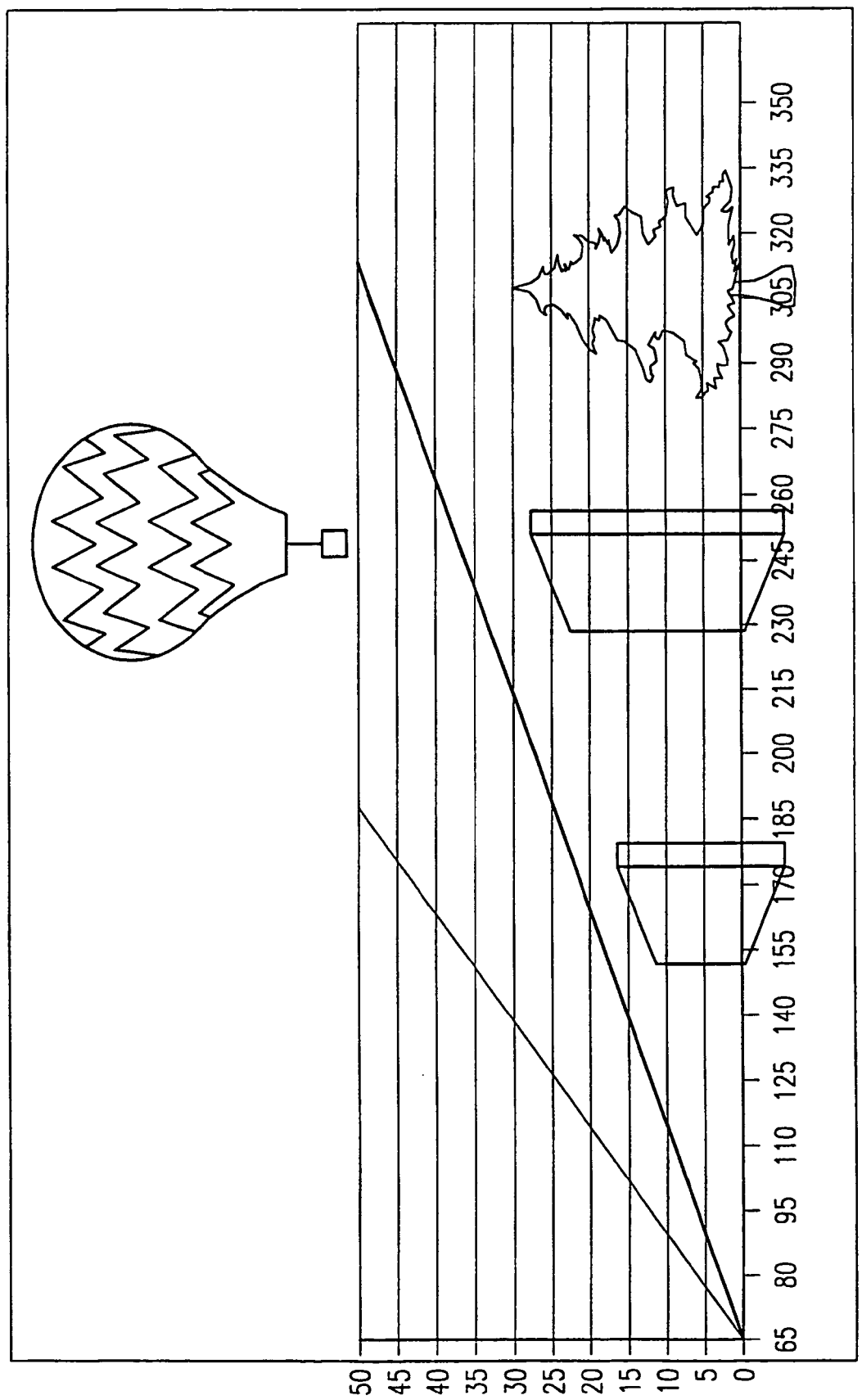
FIGS. 10–12 illustrate three different sequences of graphic displays which provide animated visual representations of the achieved level of entrainment, as determined according to one embodiment of the present invention.

Note that in an alternate embodiment, a graphical element, such as a balloon figure, may be manipulated in an appropriate way, such as rising based directly on the EP score. As illustrated in FIG. 10, a hot air balloon is illustrated rising in the sky indicating a state of entrainment. As discussed hereinbelow, the background of the scene includes a grassy field with various obstacles positioned horizontally across the screen. The balloon must rise above various heights to avoid each obstacle. This display provides a visual indication of the state of entrainment and provide a visual reward for achieving entrainment. Control of the balloon illustrates the individual's control of the emotional and/or mental state. In alternate embodiment, other graphic scenarios may be used, which accomplish a particular goal as the EP score value reflects entrainment.

In accordance with the present invention, the method is recursive, performing the various steps described above periodically, say every 5 seconds or so. According to one embodiment, the method is implemented in the form of a software program which can be stored and distributed in a computer readable medium. The software is then operated on a personal computer, or a hand held computing device, or any other medium capable of operating a software program and providing a user information display.

INDUSTRIAL APPLICABILITY

Figure 9:
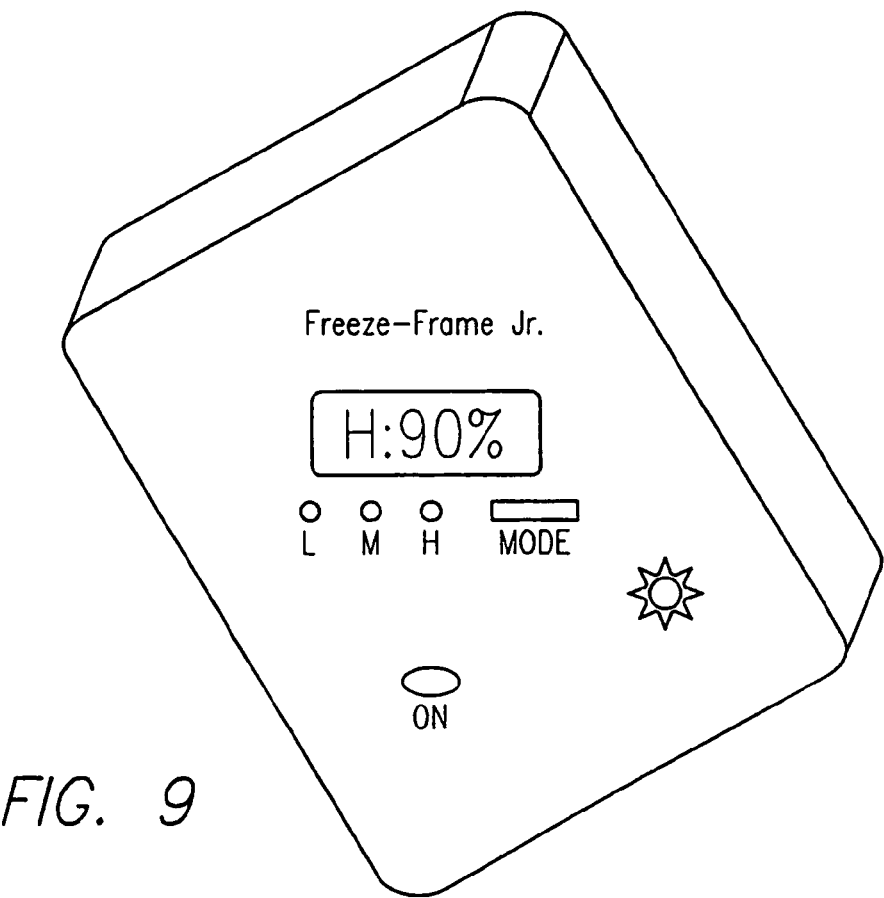
FIG. 9 illustrates a hand-held apparatus for calculating AB.

Shown in FIG. 9, is an entrainment apparatus 100 in accordance with an alternative embodiment of the present invention. In this particular embodiment, entrainment apparatus 100 is hand held unit which allows an individual to determine his or her level of entrainment. In one embodiment, entrainment apparatus 100 comprises a photo plethysmographic sensor 102, a data processing system 104, and a display 106.

In one embodiment, an individual places a finger within a receptacle located on the back of entrainment apparatus 29 which contains photo plethysmographic sensor 102. Photo plethysmographic sensor 102 senses the heart beat of the individual, by way of the finger, and sends this heart beat information to data processing system 104. Data processing system 104 collects and analyzes this heart beat data, and determines the individuals level of entrainment. A display output containing information relating to the individuals entrainment level is then generated by data processing system 104 and displayed on display 106. In one form, information relating to the individuals entrainment ratio is displayed on display 106, and a mode allows the users to review his or her low entrainment ratio, medium entrainment ratio or high entrainment ratio.

In an alternative embodiment, the sensor 102 comprises a vest or strap containing ECG electrodes. The individual places the vest on and then electrically couples it to the hand held portion of entrainment apparatus 100. The vest or strap is then used to sense the individuals heart beat and send heart beat information to data processing system 104.

Shown in FIG. 10 is a presentation format 24 produced by entrainment apparatus 10 in accordance with an alternative embodiment of the present invention. In this particular embodiment, a hot air balloon floats across a country landscape and the background scenery scrolls slowly by as the balloon floats into the sky based on the individual's entrainment level. If the individual does not maintain entrainment, the balloon sinks to the ground. Obstacles like a brick wall or a tree, as shown in FIG. 10, are presented during the course of the flight. If the individual's entrainment level is not high enough to clear one of these obstacles, the balloon's flight is impeded until an entrainment level high enough to raise the balloon above the obstacle is achieved. The calculated entrainment zone defines the balloon's climbing slope for high entrainment and for low entrainment.

Figure 11:
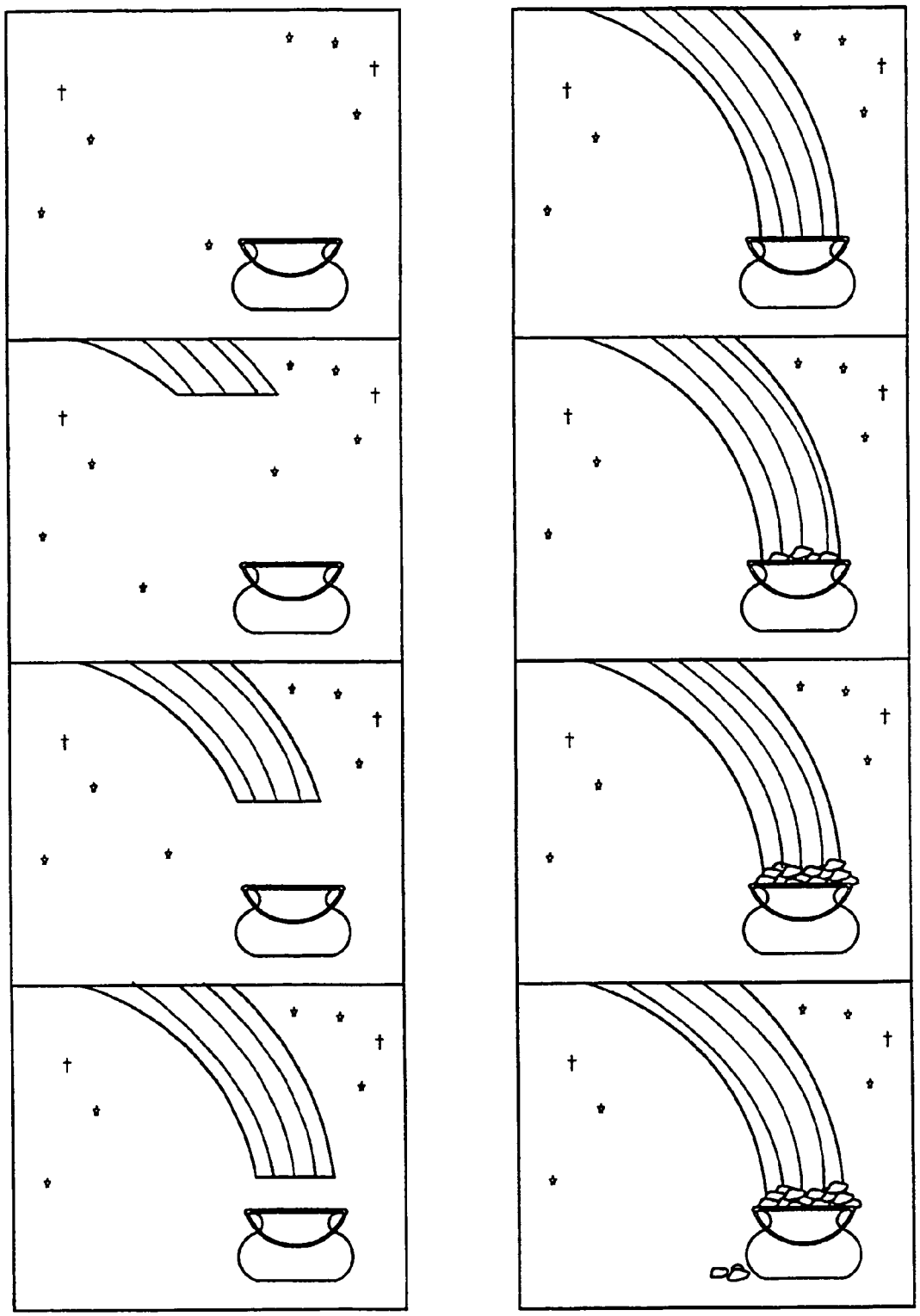

Shown in FIG. 11 is an alternative presentation format 26 produced by entrainment apparatus 10 in accordance with an alternative embodiment of the present invention. In this particular embodiment, a rainbow grows toward a pot when an individual is in a state of entrainment. Growth of the rainbow toward the pot is smooth and steady while the individual maintains entrainment, but the rainbow recedes if the individual does not maintain entrainment. Once the rainbow reaches the pot, gold coins accumulate and fill the pot if the individual continues to maintain entrainment. For example, one coin is added to the pot for each five second time period of medium entrainment and two coins are added to the pot for each five second time period of high entrainment. A total score is then presented at the end of a selected time period.

Figure 12:
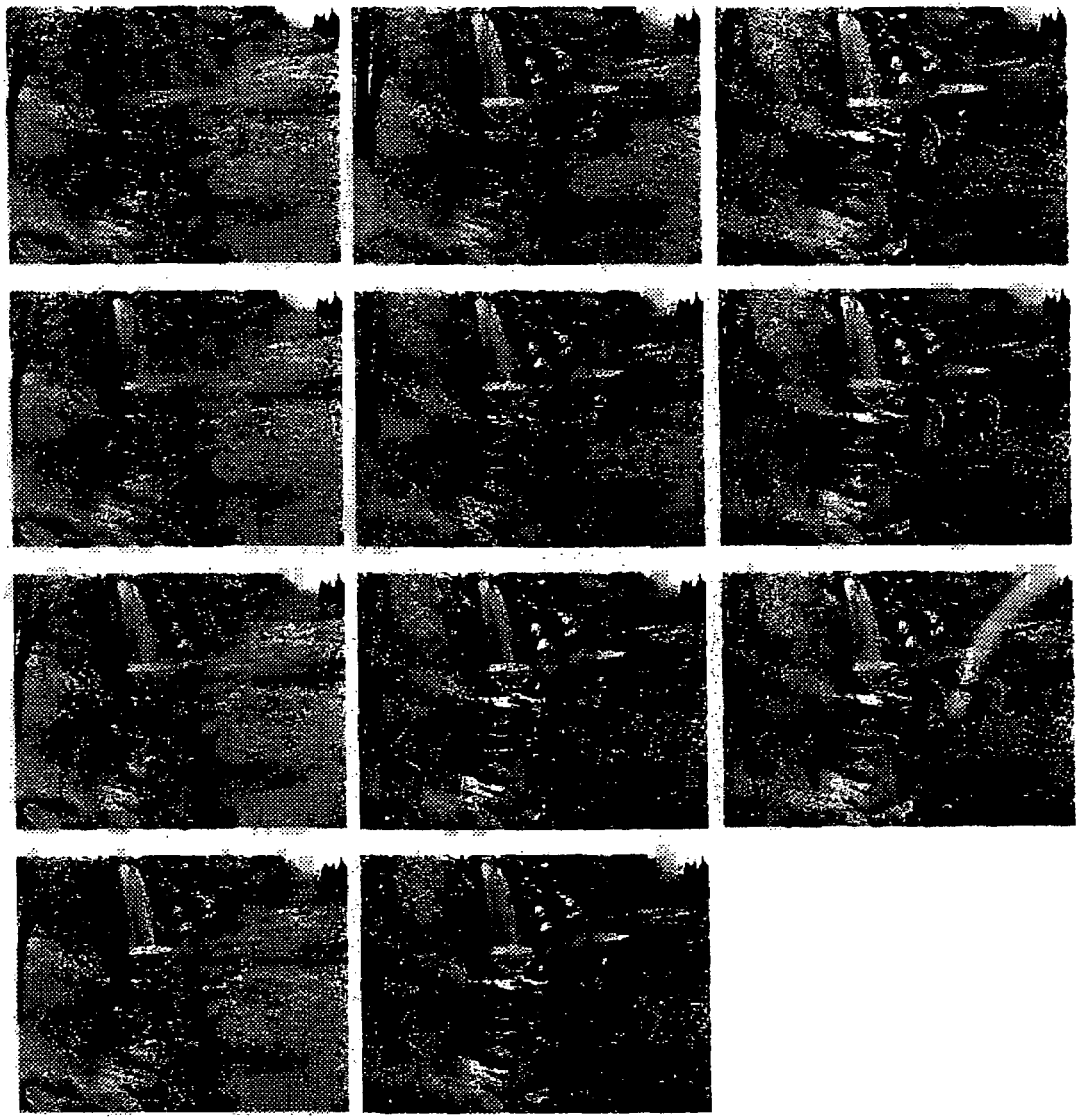

Shown in FIG. 12 is yet another possible presentation format 28 produced by entrainment apparatus 10 in accordance with an alternative embodiment of the present invention. In this particular embodiment, a nature scene changes with time as the individual maintains entrainment. For example, the scene changes for every 10 seconds that entrainment is held. If entrainment is low or not maintained the scene does not change.

Alternate embodiments may employ a variety of display formats including detailed information, graphical information, graphic images, video images, and audio images. According to one embodiment, the level of entrainment controls the volume on a music delivery system. This may be implemented based on the EP value, where the volume increases with increasing EP and decreases with decreasing EP. The system may be optimized by using music especially designed to enhance the entrainment process. Further, in one embodiment, the music changes style with entrainment level. Additionally audio controllers may provide verbal messages.

It is possible to combine the game functionality with a hand-held device in the form of a toy. In one embodiment, a crystal ball lights up and glows brighter as entrainment is maintained. The light may change color as entrainment levels are reached. Again, the color of the light is designed to optimize the entrainment method. The crystal ball may be a hand-held, or other convenient device, and may be battery-operated and/or portable to allow enhanced life performance. Alternate embodiments use toy designs and methods, such as radio-controlled toys, such as cars, trucks, and animals. The toy operation is based on the level of entrainment. In still other embodiments, stuffed animals or toys emit harmonizing sounds and music based on the level of entrainment.

For visual display embodiments, one embodiment begins with a solid background of dots, which dissolve as higher levels of entrainment are reached to reveal a graphic image, such as a 3-dimensional image. As entrainment reduces to a lower level, the dots fill the screen again.

Additionally, various computer games may use entrainment levels and/or the EP value and/or the accumulated scores as triggers to produce varied results. For example, in action games entrainment triggers access to new adventures as the game unfolds. The adventure plays out differently depending on the pattern of entrainment, i.e whether entrainment is maintained at one level, or oscillates between levels, or increases, or increases. It is possible to combine keyboard strokes and mouse and/or joystick movements to facilitate the game. In one embodiment, a locked door is only unlocked when entrainment reaches a certain level. It may be necessary to maintain entrainment at that level for a predetermined amount of time. The objects of such games may include spacecraft moving through space, animals in a jungle, race cars on a track, or any other imagery applicable to a game.

Various images are more helpful in achieving entrainment for an individual than other images. Those images are selected based on predetermined visual and auditory rhythm, and may be specific to the individual and may change from day to day. In one embodiment, a screen saver provides a visual image having a predetermined visual and auditory rhythm, and includes options for the individual to select based on personal preferences. Where feedback is provided to the screensaver program, the screen saver program may perform adjustments to optimize the effects for the individual. Our research suggests several criteria that tend to enhance entrainment. For example, circles, and shapes with rounded edges or curved lines tend to enhance entrainment better than squares, having angular, jagged, or sharp lines. Additionally, movement of the images should be slow, coherent and rhythmic, and transitions are smooth, slow and flowing. Colors and rhythms should oscillate, where the illusion is of inward and outward movement simultaneously. Movements should transition smoothly, without jarring or erratic motion.

The present invention is also applicable to sports endeavors and athletes, particularly those performing in high stress situations, such as a critical hole in golf. The games, devices, and techniques allow the athlete to practicing attaining entrainment and thus gain familiarity with this feeling state which can then be more easily accessed during actual games for improved performance. Various game embodiments may be designed for the sports enthusiast. For example, a beautiful golf course comes into view as entrainment is reached. Other games could include a golfer swinging a club or hitting a ball, where the path of flight and distance are determined by the degree of entrainment prior to the shot. In one embodiment, the game keeps score, and if not entrained, the ball goes into a sandtrap or lands in the rough or water or other hazard. Prolonged states of entrainment produces a hole in one, or other reward. Alternate embodiments may employ a similar strategy for other sports, such as baseball, basketball, football, and other popular sports.

In one embodiment, a vehicle is stuck in a traffic jam in Silicon Valley and moves proportionally to entrainment. As the car moves faster it heads for a scenic place. Note that these games may be operated on a personal computer, or other display device, or may be operated on a portable device. The portable device is highly desirable, as the value of entrainment on reducing stress and increasing the quality of life is most necessary during everyday life events. For example, a business device may combine a calculator or personal planner with the present invention, to allow a business person to utilize the device at a business meeting or negotiations without the knowledge of those around. In one embodiment, a touchpad used for manipulating a pointer on a display screen is also used to monitor heart beat data. It is also possible to have a device which is accessed by multiple persons. Here prior to beginning an activity, such as a business meeting or a sports event, each member must reach a predetermined level of entrainment for a predetermined period of time. Satisfaction of which may be indicated by a particular color light or a specified sound.

A hand-held device is applicable to education, where it effectively programs the neural network of the brain of the student allowing familiarity with the feeling of coherent and entrained states. Once developed, these states will carry over throughout adult life to influence attainment and maintenance of emotional balance and physiological coherence. By providing an easy to use format, geared to younger users, the present invention encourages them to learn how to create coherent and entrained heart rhythms. Cartoon characters, animals and popular images may be animated and provide instructions for reaching entrainment and rewards for success.

The present invention is also applicable to the medical community and medical applications. As the entrained state provides an efficient physiological state, by putting less wear and tear on the glands and organs, the present method of reaching and monitoring the entrainment state is a nonintrusive preventive medical technique. Our research suggests that by teaching individuals with certain pathologies to self-generate health, high performance heart rhythms that the bodies own regenerative systems seem to be activated and healing is facilitated. Applications of the present invention for such use include pain-control, blood pressure control, arrythmia stabilization, and diabetic management.

Research suggests that afferent input from the heart at the brain stem level modulates the ability of pain signals to transmit from the nervous system to the brain. The level of entrainment is proportional to afferent input, thereby affecting the inhibition of pain signals from the heart to the brain. A subject experiencing pain may use the present invention to reach a state of entrainment, where the pain is lessened. Further, an entrained state leads to more efficient blood flow throughout the organism and may reduce the deleterious effects of high blood pressure. In one embodiment, a game includes a visual image of the human body including arteries and major blood vessels. The level of entrainment controls the images of blood flow through the body. The display illustrates the functioning of the body internally, and indicates the specific differences in heart function during stress and high emotions, as compared to entrainment and coherence. As the rhythms of the heart become entrained, the blood flow images change to illustrate the efficient use of energy.

Still additional benefits of reaching and maintaining a state of entrainment include the efficient functioning of the autonomic nervous systems. In one embodiment, a game is used which provides visual images of the electrical signals of the nervous systems. Pulsating signals are displayed throughout the human system and are transmitted according to sensor detection from the subject. The goal of this game is to change the image such that the systems function efficiently, and to reduce or eliminate the frayed or frazzled images.

Our research has further shown that emotional self-management and physiological coherence are effective in reducing depression, anxiety, and other emotional stress, and also in improving glycemic control in diabetic populations. Additionally, maintaining an entrainment state is generally beneficial in treating anxiety, general depression, and other emotional disorders. For example, one embodiment provides a device for monitoring the autonomic balance according to the present invention prior to retiring for rest. This is particularly beneficial in the treatment of sleep disorders, and allows the subject to shift heart rhythms which tends to enhance sleep.

Additionally, the present invention is applicable to impulse control, providing training to help overcome eating disorders, anger, and/or addiction. Our research suggests that the present invention is beneficial in learning stress management, and emotional self-management. In one embodiment, a visual display is provided to illustrate other systems within the body, such as neural and hormonal systems, where signals are displayed moving from the heart to the brain. Here the effects of these signals are clearly seen, and may be controlled by attaining a state of entrainment.

Although various preferred embodiments of the present invention have been disclosed for illustrative purposes, those skilled in the art will appreciate that various modifications, additions and/or substitutions are possible without departing from the scope and spirit of the present invention as disclosed in the claims.

We claim:

1. A method comprising:
sampling a physiological measure of a subject;
tracking dynamically a power spectral density peak derived from the physiological measure and representative of a state of physiological coherency wherein an amplitude and frequency of said power spectral density peak varies over time; and
indicating that said subject is in the state of physiological coherency when said power spectral density peak is in a frequency range of between 0.03125 Hertz and 0.234 Hertz and exhibits at least a relative amplitude to one or more other peaks, wherein said state is also characterized by at least one of a sine-wave-shaped heart rhythm pattern and an increased synchronization between two or more oscillatory systems of said subject.

2. The method of claim 1, wherein sampling the physiological measure comprises sampling the physiological measure of where said physiological measure comprises heart rate variability, respiration patterns, blood pressure rhythms and a factor derived from ECG-R wave amplitudes.

3. The method of claim 1, wherein said oscillatory systems are selected from the group consisting of: heart rhythms, respiratory rhythms and blood pressure oscillations, ECG R-wave amplitude, pulse wave, impedance measures and vascular responses.

4. The method of claim 1 wherein said state of physiological coherency is further characterized by a state of entrainment between two or more of said subject's heart rhythms, respiration rhythms and blood pressure rhythms.

5. The method of claim 1 wherein said state of physiological coherency is further characterized by increased positive emotions in said subject.

6. The method of claim 1 wherein said physiological measure is a pattern usable to determine an emotional state of said subject.

7. The method of claim 1 wherein said state of physiological coherency comprises having one of a phase and frequency lock between said two or more oscillatory systems of said subject.

8. The method of claim 1 further comprises providing said subject with feedback based on said physiological measure.

9. The method of claim 8 wherein said feedback causes said subject to move closer to said state of physiological coherency.

10. The method of claim 1, wherein sampling further comprises analyzing the physiological measure in one of a frequency domain, a time domain, a period analysis and a template match.

11. The method of claim 1, wherein said relative amplitude is an amplitude ratio of said power spectral density peak amplitude to a plurality of amplitudes for said one or more other peaks.

12. The method of claim 11, wherein power spectral density peak occurs within a coherency window and said amplitude ratio is computed by i) computing a first ratio of said amplitude of the power spectral density peak to a set of lower frequency peaks located below the coherency window, ii) computing a second ratio of said amplitude to a set of higher frequency peaks located above the coherency window, and iii) multiplying said first ratio and said second ratio.

13. The method of claim 12, wherein said amplitude ratio is at least 0.6.

14. A system comprising:
sampling means adapted to sample a physiological measure of a subject; and,
a processor coupled to the sampling means, said processor to,
dynamically track a power spectral density peak derived from said physiological measure and representative of a state of physiological power spectral density wherein an amplitude and frequency of said power spectral density peak varies over time, and
determine that said subject is in the state of physiological coherency when said coherency peak is in a frequency range of between 0.03125 Hertz and 0.234 Hertz and exhibits at least a relative amplitude to one or more other peaks, wherein said state is also characterized by at least one of a sine-wave-shaped heart rhythm pattern, and an increased synchronization between two or more oscillatory systems of said subject.

15. The system of claim 14 wherein said physiological measure comprises heart rate variability rhythm, respiration patterns, blood pressure rhythms and a factor derived from ECG-R wave amplitudes.

16. The system of claim 14 wherein said oscillatory systems are selected from the group consisting of heart rhythms, respiratory rhythms and blood pressure oscillations, ECG R-wave amplitude-pulse wave, impedance measures, vascular responses.

17. The system of claim 14 wherein said state of physiological coherency is further characterized by a state of entrainment between two or more of said subject's heart rhythms, blood pressure rhythms and respiration rhythms.

18. The system of claim 14 wherein said state of physiological coherency is further characterized by increased positive emotions in said subject.

19. The system of claim 14 wherein said physiological measure is a pattern usable to determine an emotional state of said subject.

20. The system of claim 14 wherein said state of physiological coherency comprises having one of a phase and frequency lock between said two or more oscillatory systems of said subject.

21. The system of claim 14 wherein the processor is further to provide said subject with feedback based on said physiological measure.

22. The system of claim 21 wherein said feedback causes said subject to enter said state of physiological coherency.

23. The system of claim 14, wherein said process is further to analyze the physiological measure in one of a frequency domain, a time domain, a period analysis and a template match.

24. The system of claim 14, wherein said relative amplitude is an amplitude ratio of said power spectral density peak amplitude to a plurality of amplitudes for said one or more other peaks.

25. The system of claim 24, wherein the power spectral density peak occurs within a coherency window and said processor is further to compute said amplitude ratio by i) computing a first ratio of said amplitude of the power spectral density peak to a set of lower frequency peaks located below the coherency window, ii) computing a second ratio of said amplitude to a set of higher frequency peaks located above the coherency window, and iii) multiplying said first ratio and said second ratio.

26. The system of claim 25, wherein said amplitude ratio is at least 0.6.

27. A method comprising:
sampling a physiological measure of a subject;
analyzing the physiological measure in one of a frequency domain, a time domain, a period analysis and a template match;
tracking dynamically a power spectral density peak derived from the physiological measure and representative of a state of physiological coherency, wherein the power spectral density peak has a frequency in a range between 0.03125 Hertz and 0.234 Hertz; and
indicating that said subject is in the state of physiological power spectral density when said coherency peak is in the range and exhibits at least a predetermined relative amplitude to a plurality of other peaks, wherein said state is also characterized by at least one of a sine-wave-shaped heart rhythm pattern and an increased synchronization between two or more oscillatory systems of said subject.

28. The method of claim 27, wherein sampling the physiological measure further comprises sampling one or more of a heart rate variability, respiration pattern, blood pressure rhythm and a factor derived from ECG-R wave amplitudes.

29. The method of claim 27, wherein said oscillatory systems are selected from the group consisting of: heart rhythms, respiratory rhythms and blood pressure oscillations, ECG R-wave amplitude, pulse wave, impedance measures and vascular responses.

30. The method of claim 27 wherein said state of physiological coherency is further characterized by a state of entrainment between two or more of said subject's heart rhythms, respiration rhythms and blood pressure rhythms.

31. The method of claim 27 wherein said state of physiological coherency is further characterized by increased positive emotions in said subject.

32. The method of claim 27 wherein said physiological measure is a pattern usable to determine an emotional state of said subject.

33. The method of claim 27 wherein said state of physiological coherency comprises having one of a phase and frequency lock between said two or more oscillatory systems of said subject.

34. The method of claim 27 further comprises providing said subject with feedback based on said physiological measure.

35. The method of claim 34 wherein said feedback causes said subject to move closer to said state of physiological coherency.

36. The method of claim 27, wherein said predetermined relative amplitude is an amplitude ratio of said power spectral density peak amplitude to amplitudes of said plurality of other peaks.

37. The method of claim 36, wherein power spectral density peak occurs within a coherency window and said amplitude ratio is computed by i) computing a first ratio of said amplitude of the power spectral density peak to a set of lower frequency peaks located below the coherency window, ii) computing a second ratio of said amplitude to a set of higher frequency peaks located above the coherency window, and iii) multiplying said first ratio and said second ratio.

* * * * *